(12) United States Patent
Carmeliet et al.

(10) Patent No.: US 9,234,025 B2
(45) Date of Patent: Jan. 12, 2016

(54) EXTRACELLULAR ALLOSTERIC INHIBITOR BINDING DOMAIN FROM A TYROSINE KINASE RECEPTOR

(75) Inventors: Peter Carmeliet, Blanden (BE); Frederik De Smet, Leuven (BE); Joost Schymkowitz, Meensel-Kiezegem (BE); Frédéric Rousseau, Groot-Bijgaarden (BE); Corentin Herbert, Paris (FR)

(73) Assignees: SANOFI, Paris (FR); VIB VZW, Ghent (BE); LIFE SCIENCES RESEARCH PARTNERS VZW, Leuven (BE); VRIJE UNIVERSITEIT BRUSSEL, Brussels (BE)

( * ) Notice: Subject to any disclaimer, the term of this patent is extended or adjusted under 35 U.S.C. 154(b) by 188 days.

(21) Appl. No.: 13/379,822

(22) PCT Filed: Jul. 2, 2010

(86) PCT No.: PCT/IB2010/053054
§ 371 (c)(1),
(2), (4) Date: Dec. 21, 2011

(87) PCT Pub. No.: WO2011/001413
PCT Pub. Date: Jan. 6, 2011

(65) Prior Publication Data
US 2012/0094864 A1    Apr. 19, 2012

(30) Foreign Application Priority Data
Jul. 3, 2009  (EP) .................................... 09290537

(51) Int. Cl.
*C07K 14/705*  (2006.01)
*C07K 14/71*  (2006.01)
*G01N 33/566*  (2006.01)

(52) U.S. Cl.
CPC ............ *C07K 14/71* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 7,083,933 B1 | 8/2006 | Griffin | |
| 2011/0269634 A1* | 11/2011 | Perez et al. | 506/8 |

FOREIGN PATENT DOCUMENTS

| | | | |
|---|---|---|---|
| GB | WO2005121318 | * 12/2005 | ............ C12N 5/06 |
| WO | WO2005066211 | 7/2005 | |
| WO | WO2005082457 | 9/2005 | |

OTHER PUBLICATIONS

Bogoyevitch et al in "A new paradigm for protein kinase inhibition: blocking phosphorylation without directly targeting ATP binding" (Drug Discovery Today Aug. 2007: vol. 12, Nos. 15/16, pp. 622-633).*
Eglen et al in "The Current Status of Drug Discovery Against the Human Kinome" (Assay and Drug Development Technologies, Feb. 2009).*
Udugamasooriya D G et al: "A peptoid antagonist of VEGF Receptor 2 recognizes a 'hotspo' in the extracellular domain distinct from the hormone-binding site" Bioorganic & Medicinal Chemistry, Elsevier Science Ltd, GB, vol. 16, No. 12, Jun. 15, 2008, pp. 6338-6343.
Udugamasooriya D Gomika et al: "A peptoid "antibody surrogate" that antagonizes VEGF receptor 2 activity." Journal of the American Chemical Society Apr. 30, 2008, vol. 130, No. 17, Apr. 30, 2008, pp. 5744-5752.
Ivanisevic Ljubica et al: "TrkA receptor "hot spots" for binding of NT-3 as a heterologous ligand." The Journal of Biological Chemistry Jun. 8, 2007, vol. 282, No. 23, Jun. 8, 2007, pp. 16754-16763.
Maillet Emeline L et al: "A novel, conformation-specific allosteric inhibitor of the tachykinin NK2 receptor (NK2R) with functionally selective properties." The FASEB Journal : Official Publication of the Federation of American Societies for Experimental Biology Jul. 2007, vol. 21, No. 9, Jul. 2007, pp. 2124-2134.
Allegretti M et al: "Allosteric inhibitors of chemoattractant receptors: opportunities and pitfalls" Trends in Pharmacological Sciences, Elsevier, Haywarth, GB, vol. 29, No. 6, Jun. 1, 2008, pp. 280-286.
Kenakin Terry: "Collateral efficacy in drug discovery: taking advantage of the good (allosteric) nature of 7TM receptors" Trends in Pharmacological Sciences, vol. 28, No. 8, Aug. 2007, pp. 407-415.
Galandrin Segolene et al: "Distinct signaling profiles of beta(1) and beta(2) adrenergic receptor ligands toward adenylyl cyclase and mitogen-activated protein kinase reveals the pluridimensionality of efficacy" Molecular Pharmacology, vol. 70, No. 5, Nov. 2006, pp. 1575-1584.
Cowan-Jacob S W et al: "Structural biology contributions to tyrosine kinase drug discovery" Current Opinion in Cell Biology, Current Science, London, GB LNKD-DOI:10.1016/J.CEB.2009.01.012, vol. 21, No. 2, Apr. 1, 2009; pp. 280-287.
Christopoulos Arthur: "Allosteric binding sites on cell-surface receptors: novel targets for drug discovery" Nature Reviews. Drug Discovery, Nature Publishing Group, GB, vol. 1, No. 3, Mar. 1, 2002, pp. 198-210.
International Search Report and Written Opinion from PCT/IB2010/053054, dated Oct. 8, 2010.

* cited by examiner

*Primary Examiner* — Catherine S Hibbert
(74) *Attorney, Agent, or Firm* — Lathrop & Gage LLP; James H. Velema, Esq.

(57) ABSTRACT

The present invention relates to an extracellular binding domain for an allosteric inhibitor, whereby said binding domain is derived from a single membrane span tyrosine kinase receptor. More specifically, the invention relates to an extracellular domain derived from a Fibroblast Growth Factor Receptor (FGFR). It further relates to the use of this domain for the identification of similar domains in the extracellular part of other tyrosine kinase receptors, and to a screening method for identification of a small compound allosteric inhibitor.

11 Claims, 25 Drawing Sheets

A

B

A

B

C

D

A

B

A

IC50 = 28nM ± 12

B

IC50 = 121nM ± 30

A

B

A

B

C

D

A

B

Change in agadir score when mutating residue to Aspartate (D)
hPDGFRbeta_K387D    -515.11
hPDGFRbeta_L383D    -485.6

A

B

C

SEQUENCE LISTING

```
<160> NUMBER OF SEQ ID NOS: 2

<210> SEQ ID NO 1
<211> LENGTH: 39
<212> TYPE: PRT
<213> ORGANISM: Homo sapiens

<400> SEQUENCE: 1

His Val Glu Lys Asn Gly Ser Lys Tyr Gly Pro Asp Gly Leu Pro Tyr
1               5                   10                  15

Leu Lys Val Leu Lys Ala Ala Gly Val Asn Thr Thr Asp Lys Glu Ile
            20                  25                  30

Glu Val Leu Tyr Ile Arg Asn
        35

<210> SEQ ID NO 2
<211> LENGTH: 20
<212> TYPE: PRT
<213> ORGANISM: Homo sapiens

<400> SEQUENCE: 2

Leu Lys Ala Ala Gly Val Asn Thr Thr Asp Lys Glu Ile Glu Val Leu
1               5                   10                  15

Tyr Ile Arg Asn
            20
```

EXTRACELLULAR ALLOSTERIC INHIBITOR BINDING DOMAIN FROM A TYROSINE KINASE RECEPTOR

The present application claims the benefit of priority of International Application No. PCT/IB2010/053054 filed Jul. 2, 2010, which claims priority to European Patent Application No. 09290537.1 filed Jul. 3, 2009. The entire contents of each of the above documents are incorporated herein by reference.

The present invention relates to an extracellular binding domain for an allosteric inhibitor, whereby said binding domain is derived from a single membrane span tyrosine kinase receptor. More specifically, the invention relates to an extracellular domain derived from a Tyrosine kinase receptor, i.e. Fibroblast Growth Factor Receptor (FGFR), Vascular Endothelial Growth Factor Receptor (VEGFR) or Platelet Derived Growth Factor Receptor (PDGFR). It further relates to the use of this domain for the identification of similar domains in the extracellular part of other tyrosine kinase receptors, and to a screening method for identification of an allosteric inhibitor.

Cell-surface receptors represent the targets for the majority of all drugs (Overington, et al., 2006). Historically, drug discovery programs have been dominated by efforts to develop antagonists that compete for binding with endogenous ligands at orthosteric sites. In contrast, drugs that bind to allosteric sites, i.e., topographically distinct domains from those utlized by orthosteric ligands (if the target is a receptor) or substrates (if the target is an enzyme), and modulate a protein's activity have been more difficult to identify. However, recent years have witnessed an increase in the number of allosteric modulators identified for ligand-gated ion channels and G protein-coupled receptors (GPCRs) (Christopoulos, 2002; Kenakin, 2010. Surprisingly, no allosteric small compound modulators have thus far been identified for growth factor receptor tyrosine kinases (RTKs), despite the fact that this receptor superfamily is of immense biological importance and medical significance, and despite the fact that allosteric drugs can offer distinct therapeutic advantages over traditional orthosteric ligands, including greater safety and/or selectivity. To date, most therapies targeting RTKs have focussed either on monoclonal antibodies recognizing growth factor ligands, or small-molecule chemical compounds directly inhibiting the tyrosine kinase activity of the receptors.

One area—amongst others—that can benefit substantially from more effective and/or selective RTK small compound inhibitors is the field of anti-angiogenic drug therapies. VEGF-targeted anti-angiogenic agents prolong the survival of cancer patients, but their overall success is restricted by intrinsic refractoriness, escape via acquired resistance and, at least in preclinical models, stimulation of metastasis. It has been postulated that combination therapy with additional anti-angiogenic agents may help to overcome these challenges. Fibroblast growth factor (FGF)-2, the first identified angiogenic factor, is an attractive drug candidate. Indeed, FGFR signaling has been implicated in cancer and inflammatory disease (Shin et al., 2006; Eswarakumar et al., 2005; Malemud et al., 2007; Carmeliet, 2005), contributes to the tumor angiogenic switch (Presta et al., 2005; Kubo et al., 2002; Shine et al., 2006; Lavine et al., 2006), and rescues tumor vascularization and relapse upon VEGF inhibitor treatment (Casanovas et al., 2005). Nonetheless, the FGF family has not received substantial attention for anti-angiogenic drug development, in part because of the redundancy amongst the members of this superfamily of 18 ligands and 4 FGFRs (Eswarakumar et al., 2005; Beenken and Mohammadi, 2009; Cenni et al., 2005; Bossard et al., 2004; Compagni et al., 2000). Also, selective inhibitors of the FGFR tyrosine kinase have not been approved for clinical use (Dimitroff et al., 1999; McDermott et al., 2005).

SUMMARY OF THE INVENTION

Surprisingly the inventors have found that, by high-throughput screening combined with chemical optimization, the first orally active, small compound allosteric inhibitor of an RTK, namely the FGFR could be identified. This compound is called SSR128129 (abbreviated "SSR") (FIG. 3).

As illustrated by the detailed study based on SSR activity, SSR has the ability to inhibit all the members of a same family, presently the FGFRs family. As shown in the following examples, SSR is able to inhibit FGFR1 activity (FIGS. 4 and 6), FGFR2 activity (FIG. 8), FGFR3 activitiy (FIG. 9) and FGFR4 activity (FIG. 7). Thus, this allosteric inhibitor binds to an evolutionarily conserved FGFR allosteric site, situated in the extracellular domain of the receptor which is shared by different members of TKRs. This conserved site is located in the domain III of the FGFR (FIG. 11). The binding of SSR to its binding site induces "biased antagonism". The effect is confirmed by the fact that SSR binding to the allosteric binding site results in a conformational change in the receptor, especially in a determined frustrated domain. Due to the biased antagonism, a way to identify an allosteric inhibitor is provided by the use of a screening test based on phospho-signalling pathways measurements as described below. From now, SSR is the first example of an allosteric inhibitor of a RTK.

The validation of targeting such a site on the FGFR and the targeting of similar sites in other RTKs as VEGFR2 and PDGFRβ has important practical implications and will result in a significant therapeutic benefit.

The different aspects of this invention are illustrated in the detailed description of the invention and in the following examples.

DETAILED DESCRIPTION OF THE INVENTION

A first aspect of the invention is an allosteric binding site, derived from the extracellular domain of a tyrosine kinase receptor. An allosteric binding site, as used here, means a site where an inhibitor, preferably a small compound, can bind, without causing a competitive inhibition of the binding of the ligand to the ligand binding site of the receptor. Derived from, as use here, means that the allosteric binding site consists of a part of the extracellular domain, but does not include the complete extracellular domain. Preferably, the allosteric binding site is between 10 and 200 amino acids in length, more preferably between 10 and 100 amino acids, even more preferably between 20 and 50 amino acids, whereby said amino acids are part of the extracellular domain of the receptor.

A small compound, as used here, is a compound of non-polymeric nature, preferably with a molecular weight of less than 1000 D, more preferably less than 900 D, more preferably less than 800 D, more preferably less than 700 D, more preferably less than 600 D, even more preferably of less than 500 D Tyrosine kinase receptor and receptor tyrosine kinase (RTK) are, in the scope of this patent, application equivalent terms. "Tyrosine kinase receptor" is used to indicate the receptor, whereas "receptor tyrosine kinase" is used to indicate more specifically the kinase activity of the receptor.

Tyrosine kinase receptors are known to the person skilled in the art and include, but are not limited to receptors of the EGF, insulin-like growth factor, PDGF, FGF, VEGF, HGF, Trk, AXL, LTK, TIE, ROR, DDR, PKT7, RYK, CCK4, Eph and MuSK receptor families. Preferably, said allosteric binding site is derived from the extracellular domain of a TKR with Ig domain, including AXL, FGFR, MuSK, PDGFR, PTK7, ROR, TIE and VEGFR . . . ; even more preferably said allosteric binding site is derived from a TKR with a split kinase domain in the cytoplasmic domain; an preferred embodiment of TKRs according to the invention are the Fibroblast Growth Factor receptors (FGFRs), or an homolog, ortholog or paralog thereof.

"Homologs" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. "Orthologs and paralogs" encompass evolutionary concepts used to describe the ancestral relationships of genes. Paralogs are genes within the same species that have originated through duplication of an ancestral gene; orthologs are genes from different organisms that have originated through speciation, and are also derived from a common ancestral gene.

Such allosteric binding comprising SEQ ID NO.1 belongs to the FGFRs family, more specifically to the FGFR2. Preferably, said allosteric inhibitor site comprises SEQ ID N° 1, even more preferably it consists of SEQ ID N° 1.

In another aspect, the invention consists of a homolog, a paralog or an ortholog of an allosteric binding site. Preferably, the polypeptidic sequence of these homologs, paralogs or orthologs shares at least 70%, 80%, 90%, 95% or more of homology with SEQ ID NO.1.

As an example, such paralogs of allosteric binding site are present in the FGFRs family.

Especially, the allosteric binding site according to the invention is located in the domain III of the FGFRs.

In the same manner, an allosteric binding site for VEGFR2 is located in Ig domain 6 of the receptor, in a region including Lysine 609 and Lysine 648.

An allosteric binding site is also present in PDGFRβ and located in the region located near the transmembrane region, especially in Ig domain 3, in a region including Leucine 383 ans Lysine 387. Preferably, binding of an allosteric inhibitor to the allosteric binding site is inducing a biased antagonism.

A "biased antagonism", as used here, means that, for a receptor with several downstream pathways, not all the pathways are affected, or not all the pathways are affected to the same extent upon binding of the allosteric inhibitor to the allosteric inhibitor binding site. In a preferred embodiment, at least one downstream pathway is inhibited, whereas at least one other downstream pathway is unaffected.

Preferably, the allosteric binding site according to the invention comprises, preferably essentially consists, even more preferably consists of a frustrated domain.

As used herein, a "frustrated domain" means a protein domain or a fragment thereof that is not unambiguously directed towards one structural conformation; frustrated domains are known to the person skilled in the art, and the presence of frustrated domains is detected either by an ambiguous answer in one protein secondary structure prediction program; or by a contradiction in the prediction between two different protein secondary structure prediction programs. Preferentially, it is detected by the contradiction in the prediction from a protein secondary structure prediction program and the real structure as determined by protein structure detection method such as crystallization and X-ray diffraction. As a non-limiting example, a contradiction can be the indication of an α-helix with one method, and a β-sheet with another method. Proteins are minimally frustrated; however, some domains are inducing some frustration (called here "frustrated domain") and those domains are prone to induce conformational changes of the protein.

In a preferred embodiment, said frustrated domain comprises SEQ ID N° 2, preferably it consists of SEQ ID N° 2. This frustrated domain belongs to FGFRs family, especially to FGFR2.

Other frustrated domains can be identified as indicated above.

Another aspect of the invention is the use of an allosteric binding site according to the invention to induce a biased antagonism upon binding of a ligand to the binding site of the tyrosine kinase receptor in which the allosteric binding site is located. Still another aspect of the invention is the use of an allosteric binding site according to the invention to screen small compound inhibitors coming from a random library, binding to said site.

Still another aspect of the invention is a method for identification of an allosteric inhibitor binding site in the extracellular domain of a tyrosine kinase receptor, comprising the screening for the presence of frustrated domains in said extracellular domain. Methods to screen frustrated domains are known to the person skilled in the art and an example of such method is described in example 8. As a non limiting example, frustrated domains are detected by an ambiguous answer in one protein secondary structure prediction program; preferably by a contradiction in prediction between two different protein secondary structure prediction programs, even more preferably by the contradiction in the the prediction from a protein secondary structure prediction program and the real structure as determined by protein structure detection method such as crystallization and X-ray diffraction. Programs for protein secondary structure prediction are known to the person skilled in the art; as a non limiting example, such programs are described by Rost (2003). Preferably, said frustrated domain is situated in the neighborhood of said allosteric binding site; more preferably it is located not more than 20 amino acids from the border of the binding site, even more preferably not more than 10 amino acids, even more preferably it is adjacent to said binding site, even more preferably it is overlapping with the binding site, most preferably it is comprised in the binding site. After identification of possible inhibitor sites, the screening may be completed by confirmation of the function of the possible inhibitor site, by designing compounds such as small molecules, small peptides, peptidomimetics, antibodies or nanobodies that bind to the site and of which the allosteric inhibitory function can be tested.

Another aspect of the invention is a method for identification of a small compound allosteric inhibitor binding to an allosteric inhibitor site in the extra cellular domain of a tyrosine kinase receptor according to the invention comprising the comparison of two different reporters induced by two different downstream pathways dependent upon the activation of said tyrosine kinase receptor. A reporter is any gene, protein of compound that leads to a detectable signal and can be, as a non-limiting example, an antibiotic resistance gene, a toxin gene resulting in cell death, a gene encoding a fluorescent protein such as GFP, or a gene encoding an enzyme activity such as beta-galactosidase, or a protein that is phosporylated or dephosphorylated, acetylated or deacetylated or changing in conformation. In case of a repoter gene, the coding sequence is placed under control of a suitable promoter, i.e. a promoter that is induced by binding of a ligand to the receptor and consequent induction of the reporter pathway; in case of a double pathway, two different promoters are needed. As a non limiting example, comparing the phosphorylation of proteins in the presence or absence of the allosteric inhibitor will yield differences in phosphorylation due to the biased antagonism, and these differences in phosphorylation can be used as reporter.

In a preferred embodiment, identification of an allosteric inhibitor of a RTK can be carried out by performing a screening test comprising the following the steps:
  a) contacting an allosteric binding site of a RTK with an allosteric inhibitor candidate compound
  b) measuring the changes in at least two downstream pathways dependent upon the activation/inhibition of said tyrosine kinase receptor.
  c) comparing changes in the state of at least one reporter for each of the at least two different downstream pathways dependent upon the activation/inhibition of said tyrosine kinase receptor.

wherein an allosteric inhibitor is identified when, in presence of a ligand binding to the ligand binding domain of the receptor, at least one downstream pathway is inhibited whereas at least one other downstream pathway is unaffected. The change in state of a reporter depends on the reporter used, and can be, as a non-limiting example a change in phosphorylation of a reporter protein, or the switch from not induced to induced (or vice versa) of a gene. Preferably, said change in state is a change in phosphoylation state.

Preferably, the changes in the downstream pathways are performed by the measurement of the changes in the phospho-signalling pathways, including the ERK1/2 etPLCγ signalling pathways In another embodiment, an allosteric modulator of FGF-Rs can be identified using an affinity screening based on SEC-LC/MS as described below:

The SEC-LC/MS methodology is an analytical technique used for affinity screening consisting of a 2-dimensional system coupled on-line: a size exclusion chromatography coupled to a high performance liquid chromatography for the isolation followed by an electrospray ionisation—time of flight mass spectrometry for detection.

The method is based on the capacity of some compounds to interact with soluble polypeptides (including peptides, protein domains, or full length proteins). After mixing a pool of small compounds with the peptide of interest, the peptide-ligand complex induces a mass shift allowing the separation of unbound and bound small compounds by size exclusion chromatography. Then, complex is dissociated and binders are separated from the peptide and detected using a high resolution LC/ESI-TOF for accurate mass measurement (for example with a Waters LCT Premier Mass Spectrometer). A data deconvolution algorithm allows the identification of bound molecules from the mass detection analysis.

For the identification of small compound allosteric modulators of FGFRs, this technology can be applied to the extracellular domain of different FGF-Rs, either native or mutated. The native form allows the detection of all the binders to the extracellular domain. Alternativelyr allosteric modulators can ber screened by using an "open" form of the FGF-R2 helix close to the SSR binding site. Said "open" form can be obtained by the mutations Tyr328Arg-Ile329Lys that stabilizes an alpha-helix, thereby allowing sensitization to SSR binding. The mutated FGF-R2 is then used in the screening, instead of WT FGF-R2. A similar strategy can be used for screening FGF-R1, -R3 or -R4 with mutations on amino acids corresponding to Tyr328 and Ile329 in FGF-R2. The mutated form at Tyr328Asp (FGF-R2) or other FGF-Rs with a mutation at the corresponding positions can be used as control. Indeed, SSR fails to bind on the FGF-R2 that is mutated at Tyr328Asp near a hydrophobic pocket. Therefore this mutated form can be used to discard part of compounds that don't interact with targeted pocket on FGF-R2.

In all these cases, this strategy leads to the identification of small compounds able to bind on the target pocket of the peptide of interest. In a second step, the effect on the signalling in the cell has to be evaluated. Based on the phospho-signalling pathways identified with the Proteome Profiler™ Array "human phospho-kinase array kit" from R&D Systems, allosteric modulators can be checked by ELISA (on cell protein extracts or directly on cells) on their ability to inhibit FGF-2 effect on HUVEC at the phosphorylation kinase level (on PYK2, eNOS, p53, c-jun, AKT, CREB, Erk1/2) without inhibition of unaffected kinases detected with the proteome profiler.

A similar approach can be followed for other RTKs: after identification of one or more frustrated domains in the extracellular domain of the receptor, said frustrated domain can be used in a SEC-LC/MS approach to identify binders in the region of the frustrated domain. The effect of the binder on the signalling pathway can then be tested using the phosphomap approach, as described above, or any other reporter system of the pathway.

Still another aspect of the invention is a small compound compound binding to an allosteric binding site, also called "allosteric inhibitor" according to the invention, and/or identified with a method according to the invention.

"Compound" means any chemical or biological compound, including simple or complex organic and inorganic molecules, peptides, peptido-mimetics, proteins, antibodies, carbohydrates, nucleic acids or derivatives thereof.

EXAMPLES

Materials and Methods to the Examples

STD-NMR Binding Assay

Figure 1:
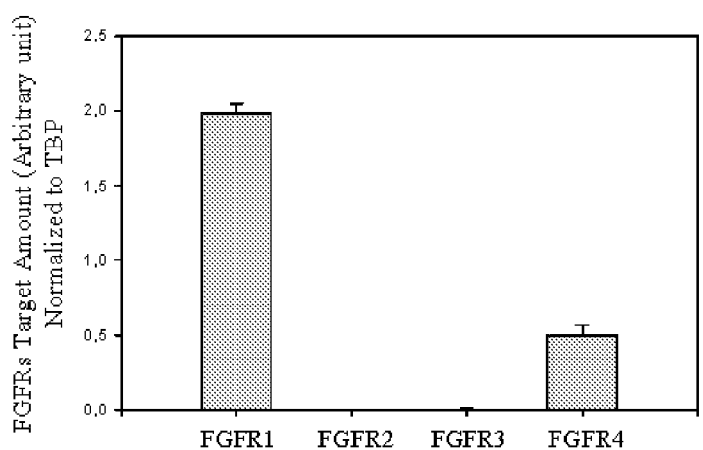
FIG. 1: A/ Quantitative PCR experiment on HUVEC shows only FGFR1 and FGFR4 expression. B/ RT-PCR analysis identified isoforms FGFR1β and FGFR4. FGFR1 is under the format of IIIc variant (C).
Figure 1:
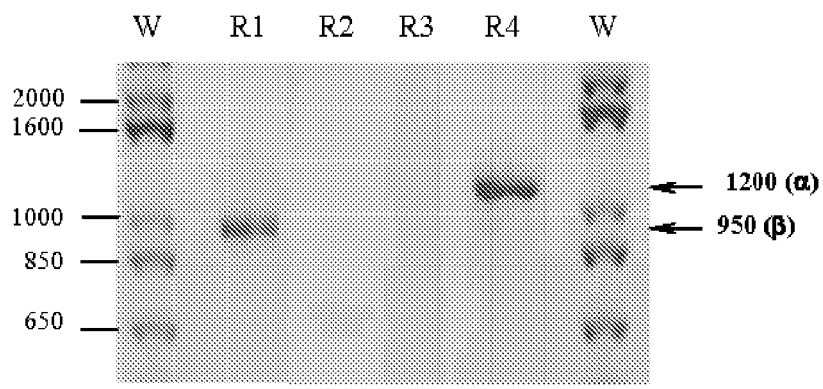
Figure 1:
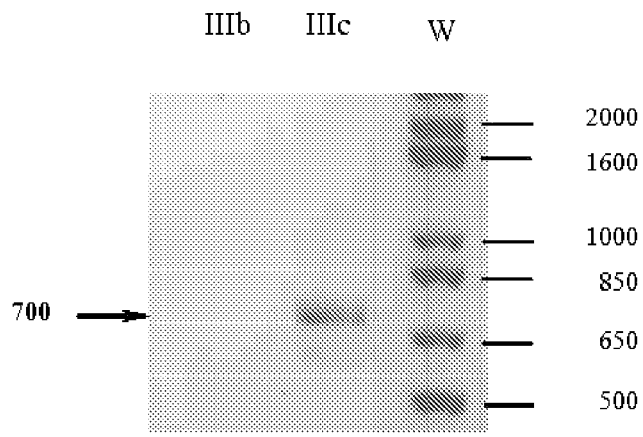

The extracellular domain (ECD; amino acids: 39-358) of the human FGFR1 gene (P11362) was PCR amplified and cloned into *E. coli* vector pETTEV (with a N-terminal His-tag followed by a TEV protease cleavage site), using NdeI and BamHI restriction sites. For protein production, the resulting plasmid (pET FGFR1 D1D2D3) was transformed into *E. coli* BL21(DE3) (Novagene). Cells were grown at 37° C. until the $OD_{600}$ reached 0.6 and recombinant protein production was induced by adding 1 mM IPTG (isopropyl-b-D-thiogalactopyranoside). After 4 hours induction, cells were harvested and stored at −80° C. until usage. The cell pellet (1 L culture) was thawed and resuspended in 50 ml buffer 1 (20 mM Tris/HCl, pH 7.5, 200 mM NaCl) containing lysozyme (2 mg), and 40 U benzonase (Merck). Cells were broken by sonification, the inclusion bodies (IB) were sedimented by centrifugation (15,000 g, 20 min, 4° C.), and the resulting pellet was washed twice with buffer 1. The IB pellet was dissolved in 20 ml denaturation buffer (6 M guanidine-HCl, 20 mM Tris/HCl, pH 8.0, 200 mM NaCl) for 40 minutes at room temperature. Insoluble debris was removed by centrifugation (30,000 g, 30 min) and the supernatant was loaded on a Ni-NTA column (Qiagen) pre-equilibrated with buffer A following the manufacturer's recommendations. The FGFR1 ECD was eluted from the column using denaturation buffer with 500 mM imidazol. Fractions containing the ECD were pooled and refolded by flash-diluting of the solubilised protein (dilution factor 1:30) into 50 mM Tris/HCl, pH 8.0, 250 mM NaCl, 0.5 M L-arginine, 2 mM EDTA, 0.02% azide followed by incubation with gentle stirring for 24 h at 4° C. The refolding mixture was centrifuged at 30,000 g for 20 min, concentrated through a YM10 membrane (final protein concentration 1 mg/ml) in an Amicon stirred cell, dialysed against 25 mM Tris/HCl, pH 8.0, 2 mM EDTA, 0.02% azide, applied to a HiTrap Heparin HP 5 ml (GE Healthcare) and eluted with a linear gradient from 0 to 2 M NaCl. Final purification of the FGFR1 ECD was achieved by size-exclusion chromatography using a Hi Load 26/60 75 pG column (GE Healthcare) equilibrated with 25 mM Tris/HCl, pH 8.0, 200 mM NaCl, 25 mM L-arginine, 2 mM EDTA, 0.02% azide. FGF1 (amino acids: 16-155) and FGF2 (amino acids 9-155) and TNF-R1α were expressed and purified. The structural integrity of the FGFR1 ECD was demonstrated by its ability to bind the heparin column (see above) and by formation of a complex with FGF1. Complex formation was analyzed by size exclusion chromatography and subsequent analysis on SDS-PAGE.

All STD- and 1D-NMR experiments were carried out on a BRUKER three-channel DRX600 and on a BRUKER four-channel DRX800 spectrometer at the standard temperature of 298 K and were referenced to the internal standard 3-Trimethyl-2,2,3,3-tetradeuteropropionate-sodium salt (TSP). Typically, NMR samples contained 0.5 ml of protein (20-300 mM) in 25 mM Tris/HCl, pH 8.0, 200 mM NaCl, 25 mM L-arginine, 2 mM EDTA, 0.02% azide (in 95% $H_2O$/5% $D_2O$). For protein ligand 1D STD NMR measurements spectra were recorded with 1 mM ligand SSR128129E (100 mM DMSO stock solution) and 40 mM protein with weak 2s RF irradiation on separated protein methyl resonances. Water suppression was carried out using the standard Bruker WATERGATE 3-9-19 sequence. NMR data were processed using the Bruker program xwin NMR software.

Isothermal Titration Calorimetric (ITC) Measurements

All calorimetric experiments were performed at 30° C. with a VP-ITC titration calorimeter (MicroCal Inc., Northampton, Mass.) as previously described[45]. Titrations involved the addition of 10 µL aliquots of 1.25 mM SSR via a rotating stirrer-syringe to the solution cell containing 1.407 mL of the 10-20 µM interacting protein (i.e. $FGFR2^{3123}$, $FGFR2^{323}$ and its described mutants and subdomains, $FGFR3^{3123}$, FGF1, FGF2 and Follistatin (as negative control) at 4 min intervals. A constant stirring speed of 300 rpm was maintained and data were fitted to the standard noninteracting one site model supplied by MicroCal, with n fixed as 1.0. All measurements were performed in 10 mM HEPES pH 7.2, 150 mM NaCl, and proteins were purified as previously described (Pellegrini et al., 2000). Mutagenesis was performed using the 'site directed mutagenesis kit' (Stratagene).

Fourier Transform Infrared Measurements

Fourier transform infrared measurements were performed using a Bruker Tensor 37 FT-IR spectrometer equipped with an AquaSpec flowcell. The sample compartment was thermostatted to 25° C., 100 spectra were averaged for a good signal to noise ratio. Proteins were purified as described above. Immediately after the gelfiltration, the proteins were dialysed overnight in the same preparation of buffer (10 mM Hepes pH 7.2, 150 mM NaCl) in the presence or absence of SSR. Dialysis buffer samples were used to substract background signal. The analysis was performed using the OPUS software package, provided by Bruker. Interpretation of the results was performed as described {Barth, 2002 #60}.

HEK293 Transfection and Erk1/2, PLCγ and FRS2 Phosphorylation Studies

HEK293 cells were either transiently of stably transfected (using FuGENE 6, Roche) with hFGFR2IIIca or hFGFR2IIIca-Y328D cloned in pcDNA3 (Invitrogen). Stably transfected cells were grown in G418 (400 µg/ml) containing medium. Before stimulation, the cells were starved overnight in DMEM (0% serum), and pre-incubated with SSR128128E at the required concentration. The cells were subsequently stimulated with FGF2 (concentration between 0.5-10 ng/ml) for 5 min at 37° C. with or without SSR or SU5402 at 1 µM. After washing with ice-cold phosphate-buffered saline containing phosphatase inhibitors (Roche), cells were lysed in RIPA buffer (Tris 30 mM HCl pH 7.5, 150 mM NaCl, 1 mM EDTA, 1% triton-X, 0.5% w/v deoxycholate, containing phophatase and protease inhibitors as described by the manufacturer (Roche)). Cell lysates were centrifuged at 12,000 g for 10 min, and the supernatants were collected. Proteins were separated on Novex polyacrylamide gels (Invitrogen, Carlsbad, Calif.) and subsequently transferred onto Hybond ECL nitrocellulose membranes (Amersham Pharmacia). Following incubation with 5% non-fat milk powder in PBS, the membranes were incubated overnight at 4° C. with the following antibodies: phospho-ERK1/2 (CST:9101), phospho-FRS2 (CST:3861), phospho-PLCγ (CST:2821) and FGFR2 (F0300, Sigma).

FGFR-Transfected BaF/3 Cells Proliferation:

The construction of BaF/3 cells used in this experiment has been described in detail in the application WO2007/080325.

Quantitative Real-Time PCR

Total RNA was isolated from HUVEC using the Trizole reagent (Invitrogen, USA) and the RNeasy Kit (Qiagen, Germany), from which cDNA was subsequently prepared using the Quantitect Reverse Transcription kit (Qiagen, Germany). Primer-sets and FAM™ dye-labeled TaqMan® MGB probes (Eurogentec, Belgium) were designed for human FGFR1, FGFR2, FGFR3, FGFR4, and TBP, and PCR reactions were carried out on a 7500 Fast Real-time PCR system (ABI, Germany). Each sample was analysed in triplicate along with specific standards and no template controls. Amplifications were carried out using 2× TaqMan® Universal PCR Master Mix, 20× Assays-on-Demand™ Gene Expression Assay Mix. Calculations of the initial mRNA copy numbers in each sample were made according to the cycle threshold (CT) method. The copy numbers of FGFR1, FGFR2, FGFR3, FGFR4, mRNA were normalized using TBP mRNA levels.

FGFR1 Phosphorylation Measurements

Rat fat-pad endothelial cells, stably transfected with hFGFR1IIIcα-Hemagluttinin, were grown to 80-90% confluency and serum starved (0.5% FBS) for 24 h. Stimulation was performed during 5 minutes with FGF2 at 2 ng/ml in combination with SSR or DMSO (as control). Cell lysates were centrifuged at 12,000 g for 10 min, and the supernatants were collected. HA-tagged proteins were immunoprecipitated by incubation of cell lysates overnight at 4° C. in the presence of agarose conjugated anti-HA antibodies. Immune complexes were washed three times with 1 ml of lysis buffer; proteins were eluted via incubation with 50 µl of 2×SDS sample buffer and boiling. Proteins were separated on Novex polyacrylamide gels (Invitrogen, Carlsbad, Calif.) and subsequently transferred onto Hybond ECL nitrocellulose membranes (Amersham Pharmacia). Following incubation with 5% non-fat milk powder in PBS, the membranes were incubated overnight at 4° C. with the following antibodies: pFGFR (CST: 3471) and FGFR1 (CST: 3472).

Anisotrophy Measurements

To assess whether SSR inhibits the binding of FGF1 to its binding pocket, we purified the entire extracellular domain of FGFR2 without Fc-tag (FGFR2$^{\Im 123}$) and measured the tumbling speed (as a parameter of anisotropy) of a fluorescent lumio-tagged FGF1 (FGF1-lumio; constant concentration of 1 µM) in the presence of varying concentrations of FGFR2$^{\Im 123}$ without (blue) or with (red) SSR (1 mM). When FGFR2$^{\Im 123}$ was added to FGF1-lumio, the tumbling speed of the ligand/receptor complex was slower than of FGF-lumio alone, because of its larger size. A large molar excess (1000 fold) of SSR failed to alter the tumbling speed of the complex, confirming that SSR does not displace FGF from FGFR.

HUVEC Proliferation

Confluent HUVEC cells are harvested and 5 10$^4$ cells in 100 µl RPMI 1640 (Invitrogen, 32404-014) with 0.5% FCS (Hyclone, SH30070.03), 2 mM glutamine, MEM non-essential amino-acid 1× (Gibco, 11140-035), MEM sodium pyruvate 1× (Gibco, 11360-039) are seeded per well in 96-well collagen 1-coated plates (Beckton Dickinson, 354650) overnight. Then, medium is removed and replace by 50 µl of medium that contains 2×FGF2 (R&D, 234-FSE-025), FGF4 (R&D, 235-F4-025) or FGF-19 (in house produced) and 50 µl of 2×SSR (200 or 600 nM). Cells were incubated in CO$_2$ chamber at 37° C. for 3 days and proliferation is evaluated by quantifying ATP content with 100 µl of "Cell Titer Glo Luminescent cell viability" kit (Promega, G7571).

HUVEC Chemotactic Migration

Confluent HUVEC cells are harvested and resuspended in RPMI 1640 (Invitrogen, 32404-014) without FCS, 2 mM glutamine, MEM non-essential amino-acid 1× (Gibco, 11140-035), MEM sodium pyruvate 1× (Gibco, 11360-039) at 0.8 10$^6$ cells/ml. 250 µl of cell solution is distributed with 4×SSR in the upper chamber of 24-wells BD Biocoat Angiogenesis System for endothelial cell migration (BD Biocoat, 354144) and 750 µl of medium in the lower chamber with FGF2 (R&D, 234-FSE-025), FGF4 (R&D, 235-F4-025) or FGF-19 (in house produced) at 67 ng/ml. Plates are incubated 22 h at 37° C. in a CO$_2$ chamber. Then, plate insert is removed, and placed in a new 24-wells plate (Falcon, 353504) that contains 500 µL of calcein (Molecular probes, C-3100) for 90 min. Then migrated cells are fluorescent and migration is measured by a luminometer with downstairs reading following 485 nm excitation and 535 nm emission.

HUVEC In Vitro Angiogenesis

Collagen/matrigel gels are prepared by distributing in each well of a chamberslide (Biocoat Cellware collagen, Type I, 8-well culturesides: Becton dickinson 354630), 160 µl of 1/6 diluted matrigel (Growth factor reduced Matrigel: Becton dickinson 356230) in collagen I (rat Tail collagene, type I: Becton dickinson 354236). Polymerisation occurs at 37° C. for 1 h. Then, 15.10$^3$ HUVEC are added per well in 400 µl EBM medium (Clonetics C3121)+2% FCS+hEGF 10 µg/ml. Endothelial cells are stimulated with 10 ng/ml of FGF2 (R&D, 133-FB-025), FGF4 (R&D, 235-F4-025) or FGF19 (R&D, 969-FG-025) for 24 h at 37° C. in a CO$_2$ chamber. Then, total length of pseudotubules is quantified using a bioimaging system (Imagenia Biocom, Courtaboeuf, France).

Western Blot Analysis of AKT Phosphorylation in HUVEC

HUVE Cells (Promocell, C-12200) are seeded in 35 mm collagen I coated disk (BD Biocoat, 354456) at 0.5.10$^6$ cells in 2 ml of EBM medium (Clonetics, CC-3121) containing 2% FBS (Clonetics, CC-4101), 10 µg/ml hEGF (Clonetics, CC-4017) from the EGM singlequots kit (Clonetics, CC-4133), 1250 ng/ml heparin (Sigma, H3149) and 375 ng/ml ECGS (BD Biosciences, 356006). At 90% confluency, cells are starved overnernight in 1.8 ml of RPMI 1640 (Invitrogen, 32404-014), 0.5% FCS, 2 mM glutamine, 1 mM non-essential amino acids (Invitrogen, 11140-050), sodium pyruvate (Invitrogen, 11360-070). The day after, cells are stimulated 10 min by 200 µl of equilibrated starvation medium that contains 10×FGF-4 (30 ng/ml; R&D, 235-F4-025) with or without 10×SSR (3 µM). Next, cells are rinsed with cold PBS and cell lysed with 75 µl RIPA that contains 2.5 mM orthovanadate and protease inhibitors cocktail (Sigma, P8340). Cell lysates were centrifuged at 12,000 g for 10 min, and the supernatants were collected. Proteins were separated on 4-20% Novex Tris-Glycine polyacrylamide gels (Invitrogen) and subsequently transferred onto nitrocellulose membranes (Invitrogen, IB3010-01). Following incubation with 5% non-fat milk powder in TBS-0.05% Tween 80, the membranes were incubated overnight at 4° C. with the anti-phosphoAKT (Ser473, CST, 4058) diluted 1000× in TBS, tween, 1% BSA. Signal of each spot is obtained following chemiluminescent detection with SuperSignal® West Dura Extended Duration Substrate (Thermo Scientific, 34076) and spot density is quantified using a BioImaging System Chemigenius2 (Syngene).

On-Cells AKT Phosphorylation ELISA

Confluent HUVEC cells are harvested and 5 10$^4$ cells in 50 µl RPMI 1640 (Invitrogen, 32404-014) with 0.5% FCS (Hyclone, SH30070.03), 2 mM glutamine, MEM non-essential amino-acid 1× (Gibco, 11140-035), MEM sodium pyruvate 1× (Gibco, 11360-039) are seeded per well in 96-well collagen 1-coated plates (Beckton Dickinson, 354650) overnight. Cells are stimulated 5 min with 100 µl equilibrated staved medium without FCS containing 20 ng/ml FGF4 and 600 nM SSR. Then, add 50 µl of PFA 8% in PBS (Polysciences, 18814) for 15 min at room temperature and wash the cells 3 times with 200 µl PBS for 2 min. Non specific sites are blocked for 1 h at room temperature with PBS, triton 0.3%, normal goat serum 0.1% (Zymed, 50-062Z) and the blocking buffer is draw-up and replaced by anti phospho-AKt (Ser473) antibody (CST, 4058) 1/500 diluted in PBS, triton 0.3% overnight. Primary antibody was then eliminate and washed 3 times with 200 µl PBS for 2 min. HRP-conjugated anti-rabbit secondary antibody (CST, 7074) is used to detect AKT phosphorylation following 1/2000 dilution in PBS, 0.3% triton for 2 h at room temperature. Then, cells are rinsed with PBS and 100 µl of HRP substrate (Uptima, UP664781) is added for 20 min in a dark room. Enzymatic reaction is stopped with 100 µl of stop buffer (Uptima, UPS29590) and OD was measured at 450 nm.

FGF2 Binding on FGFR-Transfected 300-19 Cells:

FGF2 was labeled with Alexa Fluor 488 C5-maleimide (Invitrogen, A10254) following purchaser recommendations. This AF488-FGF2 was used at 10 ng/ml in binding experiments on murine pre-B 300-19 cells transfected with FGFR1 or FGFR4 constructs in pEF6-V5/His Topo plasmids (Invitrogen). SSR (300 nM final) was pre-incubating 20 min with cells in RPMI 1640 (Invitrogen, 32404-014) with 10% FCS (Hyclone, SH30070.03), 2 mM glutamine, MEM non-essential amino-acid 1× (Gibco, 11140-035), MEM sodium pyruvate 1× (Gibco, 11360-039) and 150 mM monothioglycerol (Sigma, M6145) at 4° C. under 150 rpm agitation. Then, FGF2 (10 ng/ml final) is added for 30 min and binding is measured using a FACS Calibur flow cytometer (Beckton Dickinson). Fluorescence median for each condition is also analysed.

Cell Migration with Various Growth Factors

Cell migration was assessed by a modified Boyden chamber assay, by using 24-well inserts containing 8 µm pore size transwell permeable supports with a polycarbonate membrane (Costar, Corning Inc.). Exponentially growing cells were starved in 0.2% FBS containing medium for 16 hours and resuspended at $5 \times 10^5$ cells/ml in the same low serum medium. 100 µl of the cell suspension were seeded in the upper chamber, while chemoattractants and/or SSR were placed in the lower chamber. Chemoattractants tested include: human PDGF-BB, IGF-I, PlGF, EGF, all at 100 ng/ml, in the presence or absence of SSR (1 µM). 10% FBS containing medium was used a positive control. After 6 hours incubation at 37° C., cells on the upper side of the membrane were scraped using a cotton swab, while migrated cells on the lower surface were fixed with 1% paraformaldehyde in PBS and nuclei stained with DAPI for quantification using a fluorescent microscope. Quanitifcation is performed by making 5 random images at a magnification of 10× and by counting the number of nuclei.

PANCO2 Proliferation and Migration:

Cell proliferation was analysed on exponentially growing cells that were starved for 16 hours in 100 µl RPMI 1640 (Invitrogen, 32404-014) with 0.2% FBS (Hyclone, SH30070.03), 2 mM glutamine, MEM non-essential amino-acid 1× (Gibco, 11140-035), MEM sodium pyruvate 1× (Gibco, 11360-039) and seeded at 4,000 cells/well in 96-well microplates. After exposure to mitogens and/or SSR for 72 hours, cell proliferation was assessed with the use of the CellTiter 96 AQueous One Solution Cell Proliferation Assay (Promega, Madison, Wis., USA) according to manufacturer's instructions. Cell migration was assessed by a modified Boyden chamber assay, by using 24-well inserts containing 8 µm pore size transwell permeable supports with a polycarbonate membrane (Costar, Corning Inc.). Exponentially growing cells were starved in 0.2% FBS containing medium for 16 hours and resuspended at $5 \times 10^5$ cells/ml in the same low serum medium. 100 µl of the cell suspension were seeded in the upper chamber, while chemoattractants and/or SSR were placed in the lower chamber. 10% FBS containing medium was used a positive control. After 6 hours incubation at 37° C., cells on the upper side of the membrane were scraped using a cotton swab, while migrated cells on the lower surface were fixed with 4% formaldehyde and nuclei stained with DAPI for quantification.

B9 Myeloma Cells Proliferation:

Cell proliferation was analysed on exponentially growing cells that were starved for 16 hours in IMDM (Invitrogen, 31980048), 0.2% FBS, 2 mM glutamine containing medium and seeded at 4,000 cells/well in 96-well microplates. After exposure to mitogens and/or SSR for 72 hours, cell proliferation was assessed with the use of the CellTiter 96 AQueous One Solution Cell Proliferation Assay (Promega, Madison, Wis., USA) according to manufacturer's instructions.

Alphascreen Surefire Assay

Day 0: plate HEK293:mVEGFR2wt or HEK293:PDGFR-βcells at 10000 cells/well (96 well plate Cell binding Costar) and allow to attach Overnight Day 1: starve cells in DMEM (0% serum) for 3 h minimum; prepare mixture of 50 ng/ml of VEGF164 or PDGF-BB in DMEM (0% serum) and stimulate for 5 or 15 minutes; Lyse cells in lysis buffer from SureFire assay (Perkin Elmer): lyse cells in 50 µl of buffer, stir plate for 10 min at RT and then freeze at −20° C. until further use; make mixture of lysis buffer with protein and analyze with pERK1/2, total ERK1/2 and a custom designed pPLCγ and total PLCγ according to manufacturers instructions.

Example 1

Identification of SSR128129E as an Allosteric, Multi-FGFR Inhibitor

The objective of this study was to develop low molecular weight chemical compounds that bind to the FGFR extracellular domain (ECD) and inhibit FGFR signaling. Given that it is challenging to envisage how a small compound could interact with a much larger polypeptide (i.e. FGF) via simple steric hindrance for the orthosteric site, multiple ligand binding assay formats were utilized to determine whether any identified compounds were acting orthosterically of via an allosteric mechanism. We initially developed a high-throughput scintillation proximity binding assay (SPA) to identify compounds that inhibit the binding of $^{125}$I-FGF2 to FGFR1-ECD, consisting of the three Ig-like domains D1-3, coupled to a Fc-fragment (FGFR1$^{3123}$/Fc). After screening >20,000 compounds and chemical optimization, one compound, SSR128129E (abbreviated as "SSR" from here on), inhibited $^{125}$I-FGF2 binding. In additional SPA assays, SSR acted as a multi-FGFR inhibitor, blocking the binding of different FGF ligands to various FGFRs while not inhibiting the binding of >100 distinct ligands with related structural homology or entirely different chemical composition to their cognate receptor; this finding was suggestive either of a competitive (orthosteric) mechanism, or else an allosteric interaction characterized by high negative cooperativity (Christopoulos and Kenakin, 2002).

Figure 5:
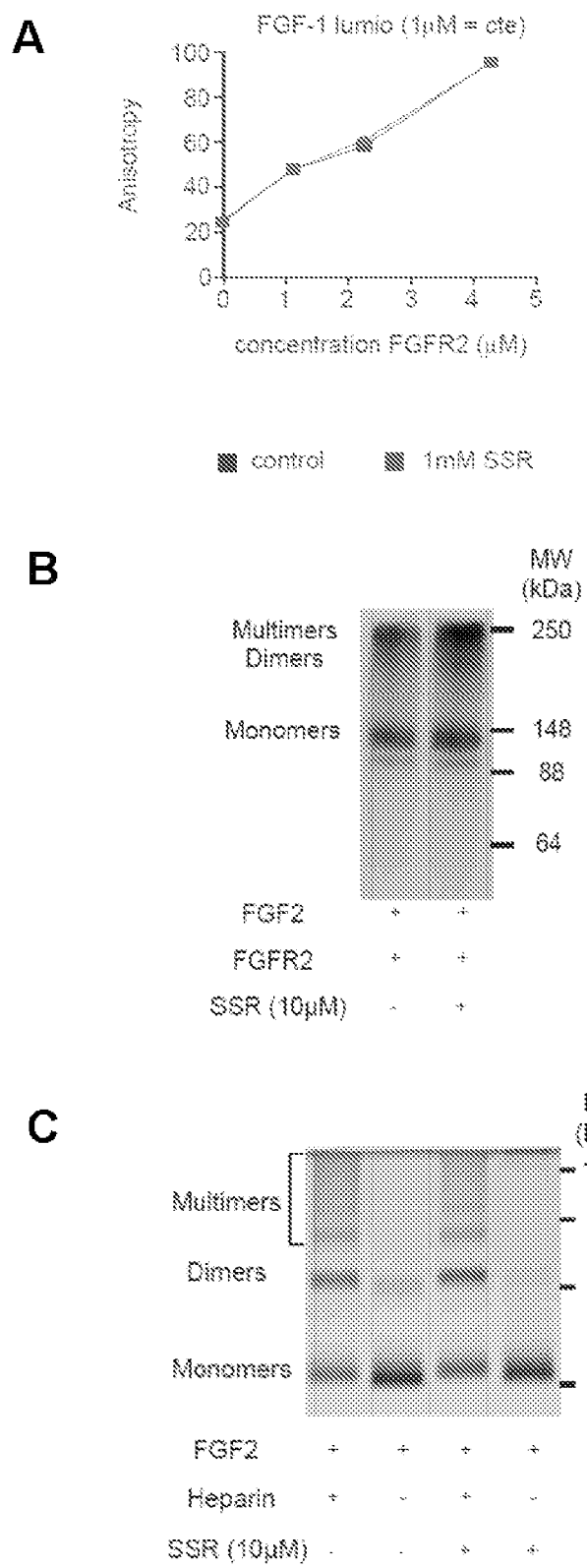
FIG. 5: A/ Binding of a fluorescent lumio-tagged FGF1 (FGF1-lumio) to a purified ECD of FGFR2 without the Fc-tag (FGFR2∂123), by measuring the tumbling speed as a parameter of anisotropy. No direct competition between SSR and FGF1-lumio is observed. B/ SSR isn't able to inhibit FGFR2 multimerization or c/ FGF2 dimerization.

One hallmark of allosteric interactions is the phenomenon of 'probe-dependence' i.e., variations in the magnitude and direction of an allosteric interaction depending on the nature of the orthosteric ligand-receptor complex with which the modulator is interacting (May et al., 2007). To determine whether the effects of SSR on $^{125}$I-FGF2 binding in the SPA were dependent on the configuration of the engineered FGFR/Fc fusion protein plated on an artificial substrate, we next studied whether SSR inhibited the binding of a fluorescent lumio-tagged FGF1 (FGF1-lumio) to a purified ECD of FGFR2 without the Fc-tag (FGFR2$^{3123}$), by measuring the tumbling speed as a parameter of anisotropy. When FGFR2$^{3123}$ was added to FGF1-lumio, the tumbling speed of the ligand/receptor complex was slower than of FGF-lumio alone because of its larger size. If SSR inhibited ligand binding, the tumbling speed should increase again. However, even at >1,000 fold molar excess, SSR failed to alter the tumbling speed of the complex indicating a lack of direct competition between SSR and FGF1-lumio (FIG. 5A). Finally, binding assays with I$^{125}$-FGF2 on human umbilical vein endothelial cells (HUVECs) or porcine aortic endothelial cells overexpressing FGFR1 (PAE-FGFR1) also revealed that SSR (even at high µM concentrations) was unable to inhibit I$^{125}$-FGF2 binding to its receptor when the latter is expressed in its more natural conformation in intact cells; a neutralizing αFGF2 antibody, however, was effective. In this latter experimental paradigm, and in contrast to the SPA, SSR also failed to antagonize the binding of additional FGF ligands to other FGFRs (i.e. FGF2 or FGF4 to FGFR2; FGF2 to FGFR4).

Collectively, these results indicated that the inhibitory activity of SSR on the binding of FGF ligands was highly dependent on the conformation of the FGFR, and inconsistent with a simple competitive mechanism relying on steric hindrance for an overlapping binding domain. The ability of small compound allosteric modulators to differentially affect the binding of orthosteric ligands depending on the assay conditions, as noted herein for the FGFR, has previously been reported in the field of GPCRs (Litschig et al., 1999; Price et al., 2005). Presumably, the FGFR1$^{3123}$/Fc exists in a conformation that allows the transmission of a negative allosteric effect on the affinity of $^{125}$I-FGF2 by the binding of SSR, whereas the absence of the Fc tag, or the expression of the entire intact receptor in its native environment, do not.

Example 2

SSR is an Allosteric and Multi-FGFR Inhibitor

Figure 2:
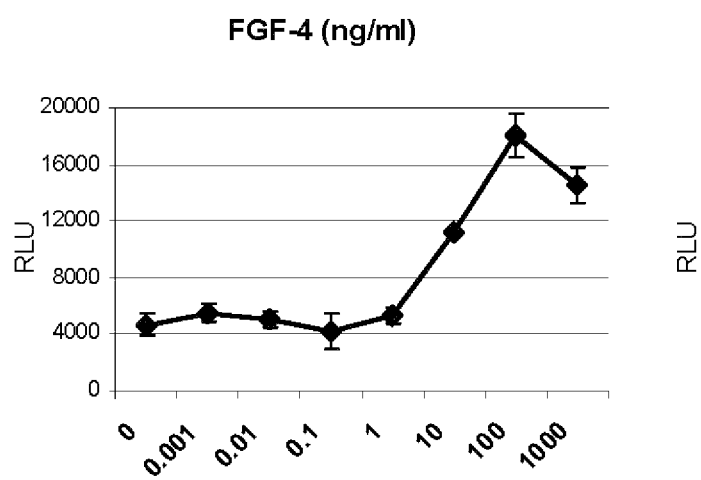
FIG. 2: BaF/3 cells transfected with FGFR1βIIIc-hMpl are able to proliferate when inserted FGFR is activated. Only FGF4 (A) is able to induce FGFR1βIIIc while FGF19 is not (B).
Figure 2:
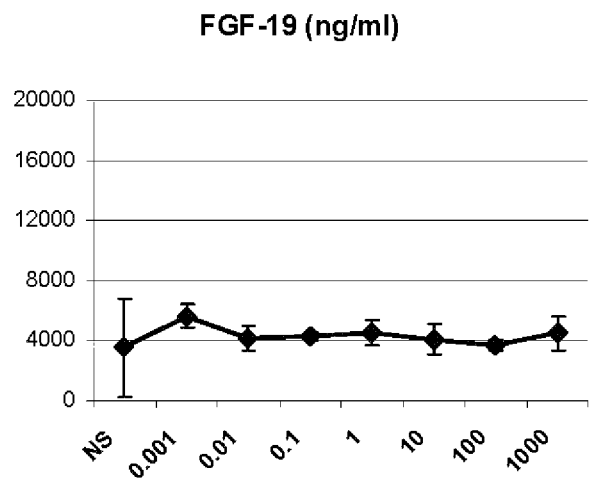
Figure 3:
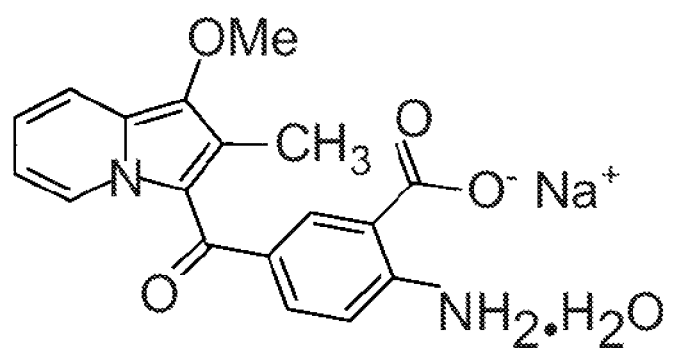
FIG. 3: SSR compound representation

Because FGFR expression analysis on HUVEC cells (C-12200, Promocell) by quantititative PCR (FIG. 1A) and RT-PCR using specific primers to detect FGFR gene expression (FIG. 1B) and FGFR1 variants (FIG. 1C) demonstrated only the expression of FGF-R4 and FGF-R1β3c, we first used HUVE Cells to study the antagonistic activity of SSR on different FGFR. FGF19 is known to stimulate specifically FGFR4, while FGF4 (but not FGF19) activates only FGF-R1 in BaF/3 cells transfected with the FGFR1-hMpl fusion protein (FIG. 2A) while FGF19 can't (FIG. 2B). So, FGFR1 and FGFR4 in HUVECs can be stimulated with FGF4 and FGF19 respectively.

Figure 4:
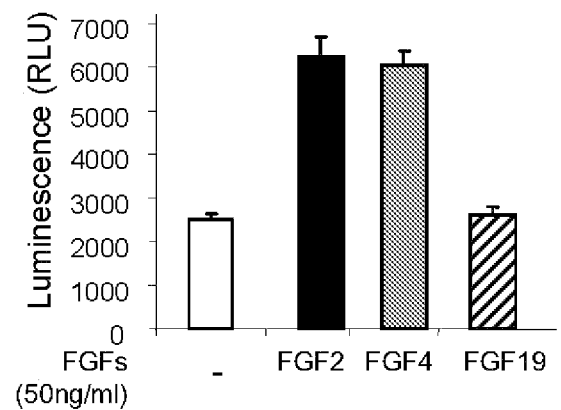
FIG. 4: Study on SSR activity on endothelial cells proliferation. A/ only FGF2 and FGF4 stimulate HUVEC proliferation indicating that FGFR1 drives proliferation in these cells. B/ SSR inhibits FGF2-induced HUVEC proliferation indicating FGFR1 antagonism by SSR. C/ In Rat Fad Pad Endothelial Cells (RFPEC) transfected with FGFR1, FGF2 induced FGFR1 autophosphorylation that is only partially inhibited with SSR even at high doses. D/ This inhibition is not due to a competitive effect of SSR on FGF2 binding in PAEC transfected FGFR1 or in HUVEC.
Figure 4:
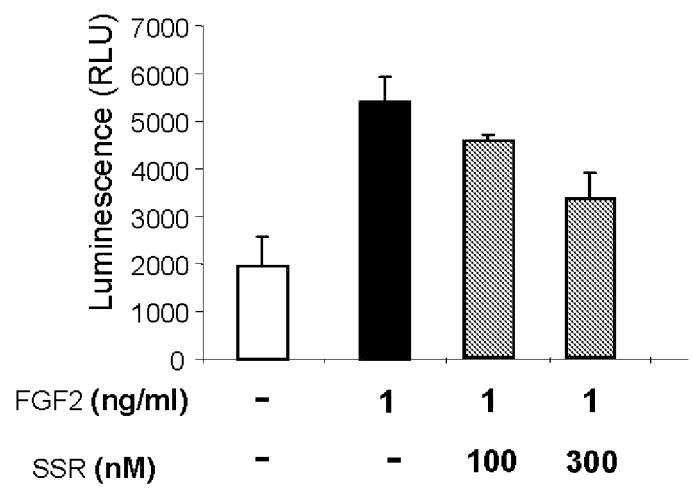
Figure 4:
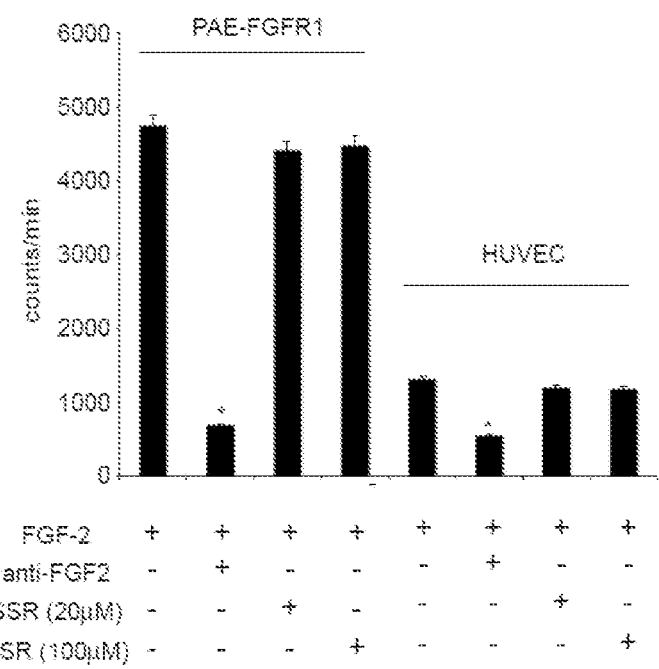

HUVEC proliferation is stimulated with FGF2 and FGF4 but not with FGF19 (FIG. 4 A) suggesting that HUVEC proliferation is under the control of FGFR1. SSR is able to inhibit FGF2-induced HUVEC proliferation indicating that SSR inhibits FGFR1β3c receptor (FIG. 4B). Binding assays with $I^{125}$-FGF2 on human umbilical vein endothelial cells (HUVECs) or porcine aortic endothelial cells overexpressing FGFR1 (PAE-FGFR1) further revealed that SSR (even at high μM concentrations) was unable to inhibit $I^{125}$-FGF2 binding to its receptor. A neutralizing αFGF2 antibody, however, was effective (FIG. 4D). We also analysed whether SSR inhibited autophosphorylation of FGFR, a critical step in FGFR signaling. Immunoprecipitation of FGFR1 expressed in rat fat-pad endothelial cells, followed by immunoblotting of phosphorylated FGFR1 revealed that FGF2-induced FGFR1 tyrosine phosphorylation was highly reduced by SSR in the nanomolar concentration range (FIG. 4C). Notably, even at high doses, SSR does not completely eliminate FGFR1 tyrosine phosphorylation, leaving a low residual level (FIG. 4C). SSR effect on lumio-tagged FGF1 binding on FGFR2 extracellular domain has been analysed and SSR doesn't inhibit FGF1/FGFR2 interaction (FIG. 5A). In the same way, SSR is not able to inhibit FGFR2 or FGF2 dimerization (FIGS. 5B and 5C).

Figure 6:
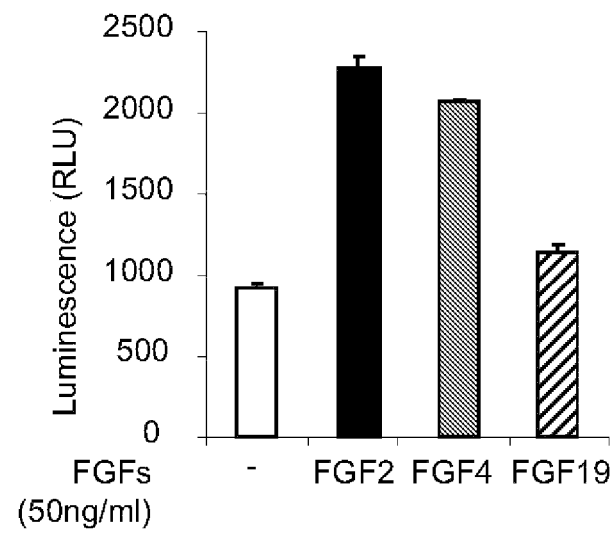
FIG. 6: Study on SSR activity on endothelial cells chemotactic migration. A/ only FGF2 and FGF4 stimulate HUVEC migration indicating that FGFR1 drives proliferation in these cells. B/ SSR inhibits FGF2-induced HUVEC chemotactic migration corresponding to its antagonistic affect on FGFR1.
Figure 6:
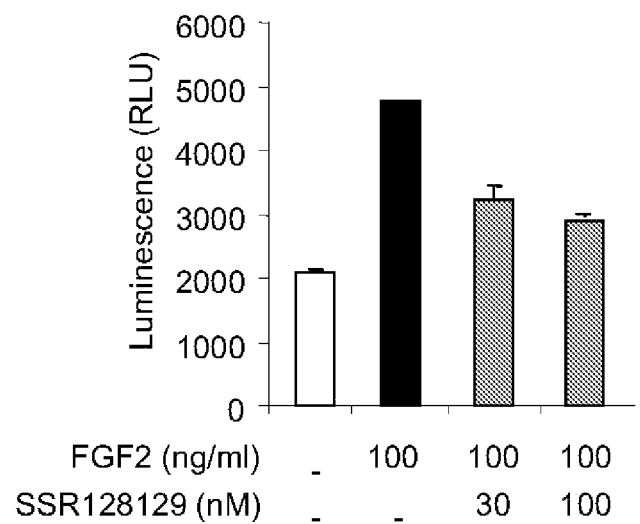

Migration of HUVECs was also stimulated by FGF2- and FGF4 but not by FGF19 (FIG. 6A). SSR, in this context, is also able to inhibit FGFR1 activity leading to reduction of FGF2-induced HUVEC chemotactic migration (FIG. 6B).

Figure 7:
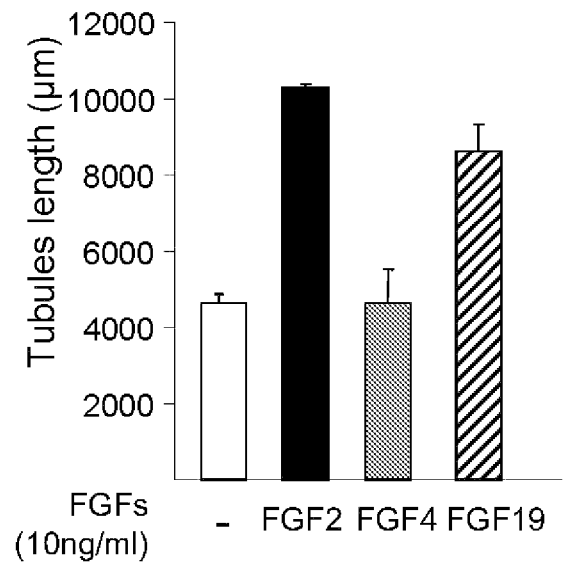
FIG. 7: Study on SSR activity on endothelial cells in vitro angiogenesis. A/ only FGF2 and FGF19 stimulate HUVEC angiogenesis indicating that FGFR4 controls this differentiation step in these cells. B/ SSR inhibits FGF2-induced HUVEC in vitro angiogenesis corresponding to its antagonistic affect on FGFR4.
Figure 7:
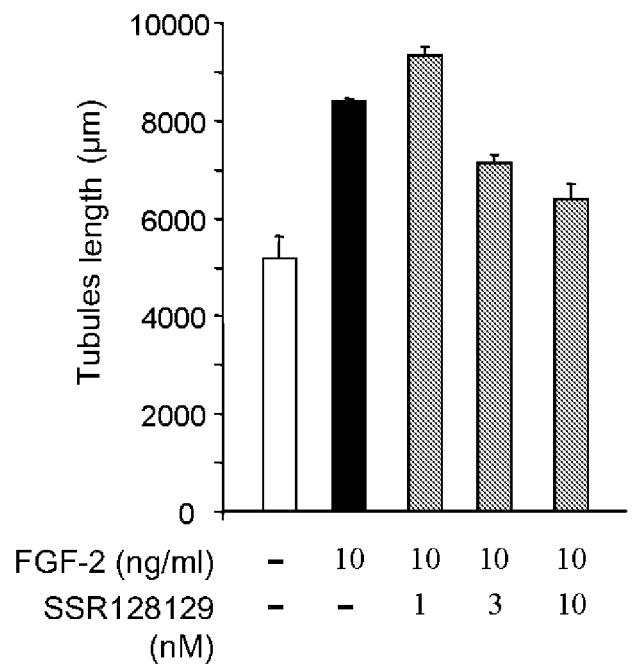

Conversely, in vitro angiogenesis is stimulated by FGF2 and FGF19 while FGF4 is inactive suggesting that FGFR4 controls in vitro angiogenesis in this assay (FIG. 7A). At low nanomolar range, SSR blocks FGF2-induced HUVEC angiogenesis demonstrating that SSR is able to inhibit FGFR4-controlled cellular process (FIG. 7B).

Figure 8:
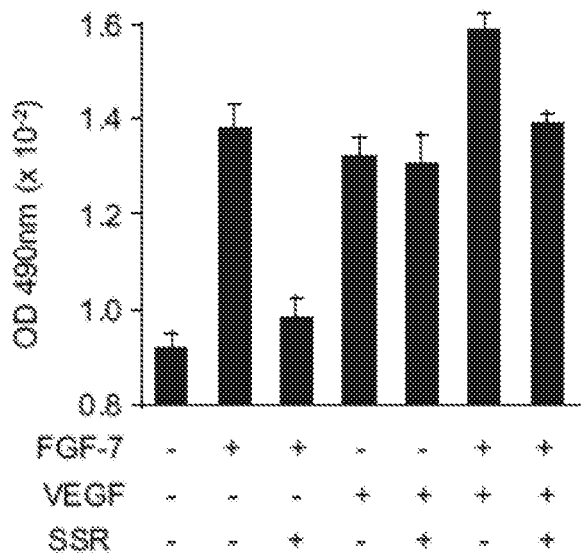
FIG. 8: Study on SSR activity on PANC02 proliferation and migration. PANC02 cells proliferate (A) or migrate (B) under FGF7 stimulation with or without VEGF suggesting a FGFR2IIIb dependence of the system. SSR inhibits FGF7-induced PANC02 proliferation and FGF7+VEGF-induced cell migration showing its ability to inhibit FGFR2IIIb.
Figure 8:
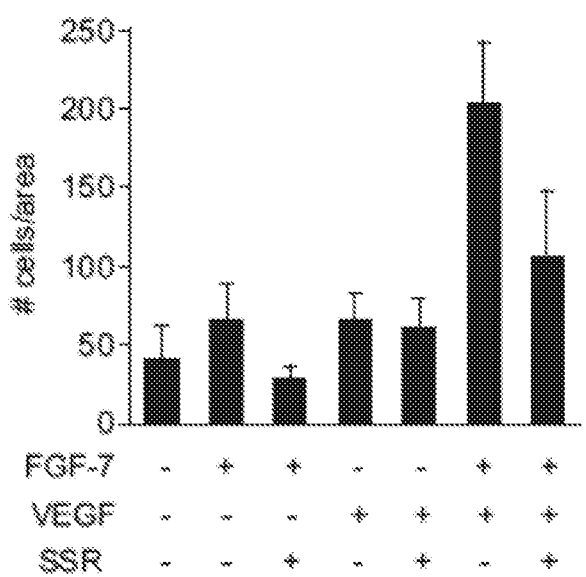

In order to evaluate SSR activity on FGFR2 and on the FGFR2-IIIb variant, proliferation and migration of PANC02 cells have been used because these cellular responses can be stimulated by 100 ng/ml FGF7 (FIGS. 8A and 8B), a specific ligand for FGFR2-IIIb. FGF7 induction, with or without VEGF, is blocked by 100 nM SSR addition showing that SSR is able to inhibit FGFR2 receptor and 3b variant (FIGS. 8A and 8B).

Figure 9:
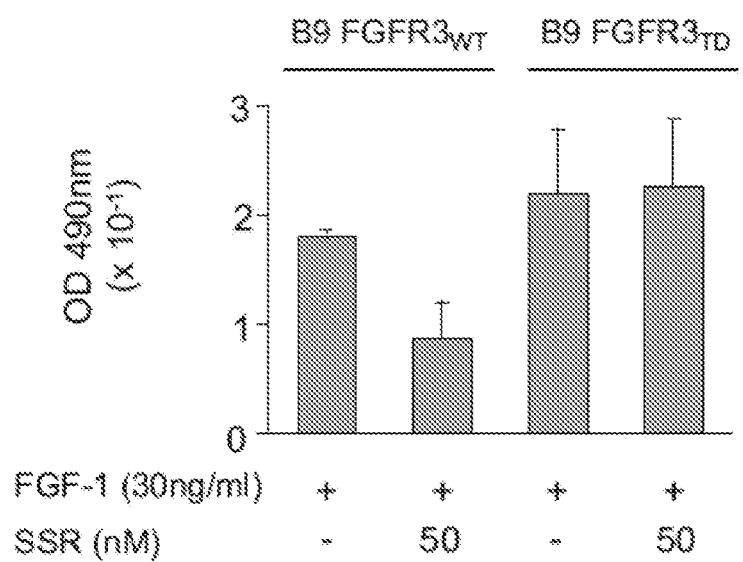
FIG. 9: Study on SSR activity on B9 myeloma cells proliferation. A/ FGF1 induces B9 myeloma cells proliferation via FGFR3 and SSR inhibits this stimulation indicating that SSR is able to block FGFR3. B/ Nevertheless, SSR isn't able to inhibit proliferation of B9 cells transfected with an autoactive FGFR3 mutant (kinase domain is constitutively phosphorylated). These results indicate an extracellular effect of SSR.

For studying SSR effect on FGFR3, the proliferation of B9-myeloma cells, expressing either FGFR3$_{WT}$ or FGFR3$_{TD}$ (a constitutively activated FGFR3 variant induced by the K650E mutation, even in the absence of any ligand; Truedel et al; blood 2006), was assayed by stimulation with FGF1 (25 ng/ml). While the B9-FGFR3$_{WT}$ cell line could be induced by FGF1 and inhibited by 0.1 μM of SSR (FIG. 9), the B9-FGFR3$_{TD}$ cell line was insensitve to SSR (FIG. 9) indicating that SSR can inhibit FGFR3 receptor and confirming that SSR doesn't act on kinase domain of FGFR.

All together, these results indicate that SSR is able to inhibit all FGFR isoforms (FGFR1, R2, R3 and R4) and FGFR variants.

Example 3

SSR is not able to Inhibit Cell Responses Induced by Other Growth Factors

Since SSR differentially inhibited FGF-dependent signaling efficacy, we next investigated whether it also affects FGF-dependent cellular responses in vitro. Using HUVECs, SSR inhibited the chemotactic effects of FGF2.

Figure 10:
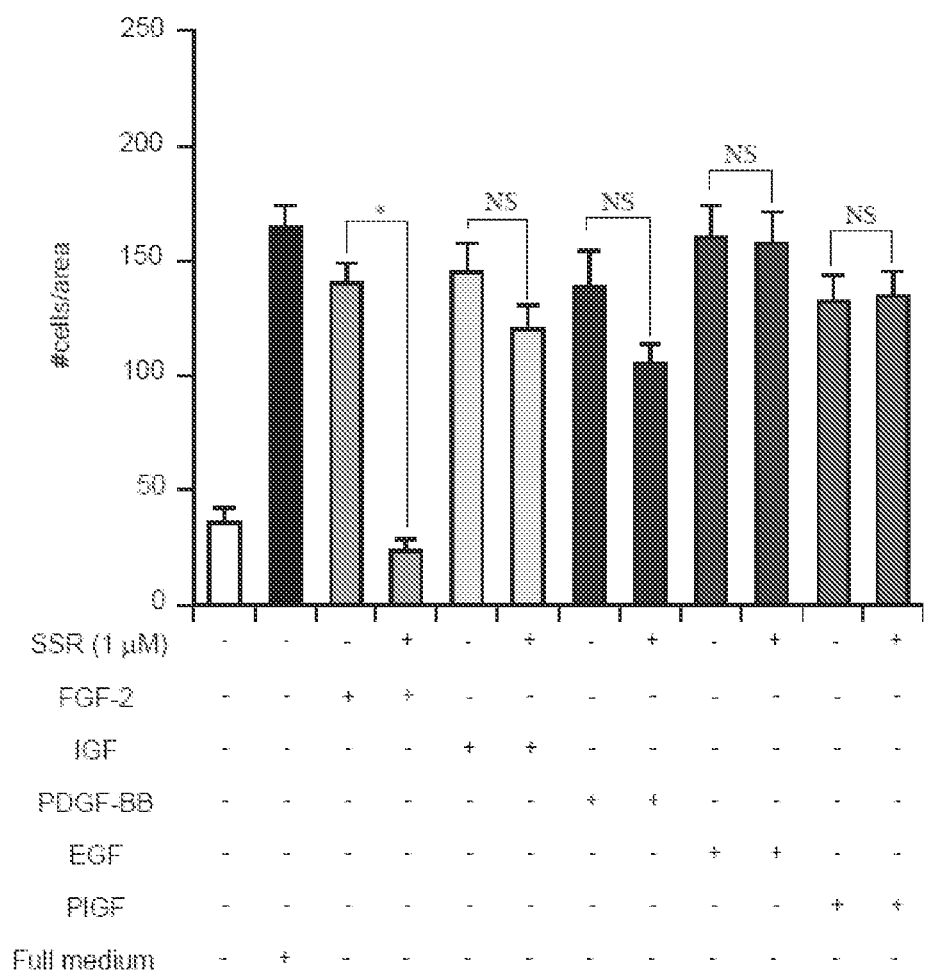
FIG. 10: HUVEC migration assay in which SSR is unable to significantly inhibit cell migration induced by various growth factors such as IGF, PDGF-BB, EGF or PlGF. SSR is specific for FGFR and only blocks FGF-induced HUVEC migration.

SSR did not affect cellular responses induced by PlGF, EGF, PDGF-BB and IGF, which are all known to activate members of the tyrosine kinase receptor family (FIG. 10).

Example 4

Figure 11:
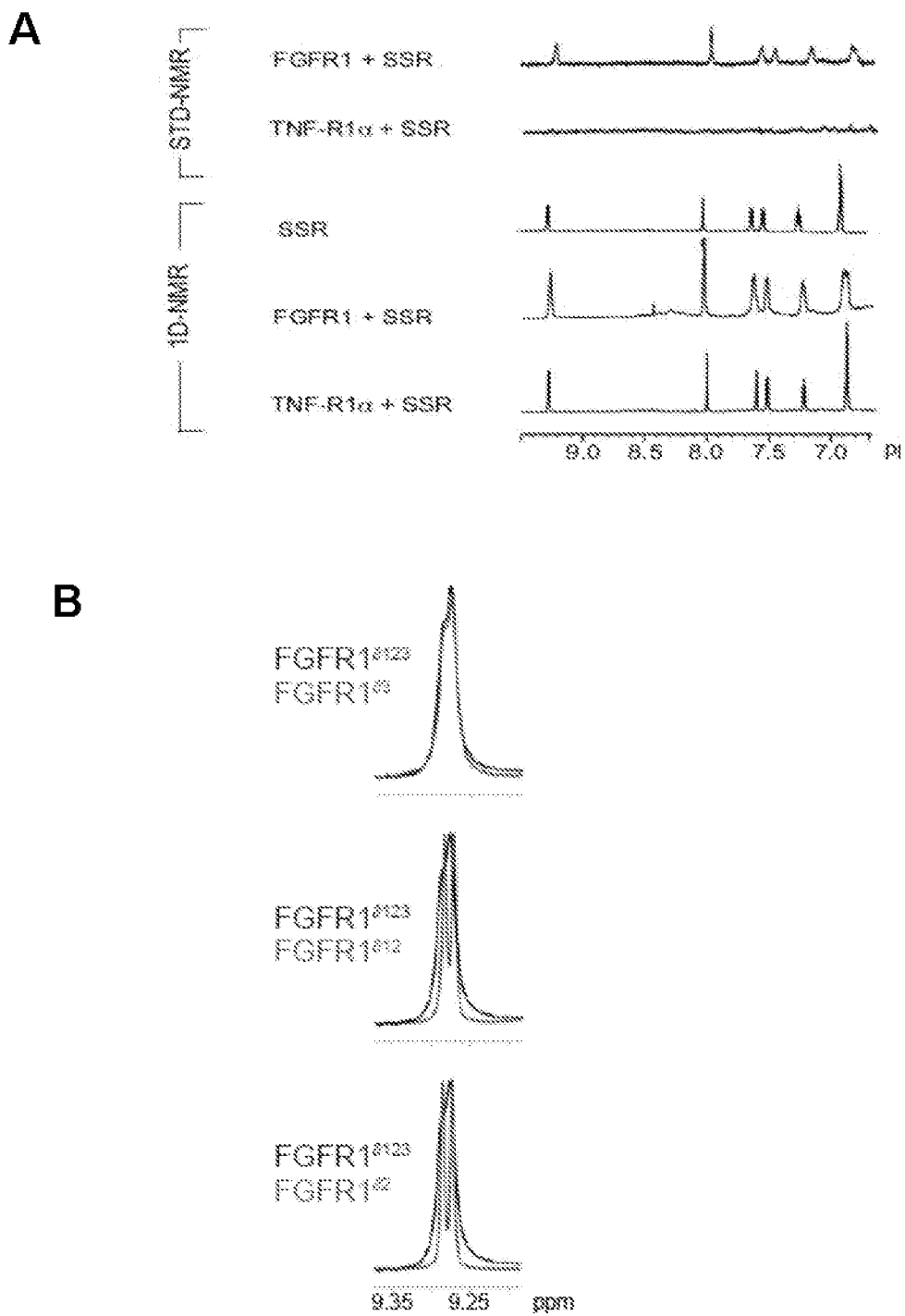
FIG. 11: NMR studies showing SSR binding on FGFR domain III. A/ 1D- and STD-NMR analysis of SSR binding on FGFR1 extracellular domain. No saturation is observed with control TNFR1α. B/ 1D-NMR study of SSR binding on different FGFR1 domains demonstrate that spectra obtained with FGFR1 full length and with FGFR1 domain II are similar suggesting an interaction site in domain III. C/ Isothermal titration calorimetric showing ability to SSR to bind on FGFR2 and FGFR3 (D) extracellular domain.
Figure 11:
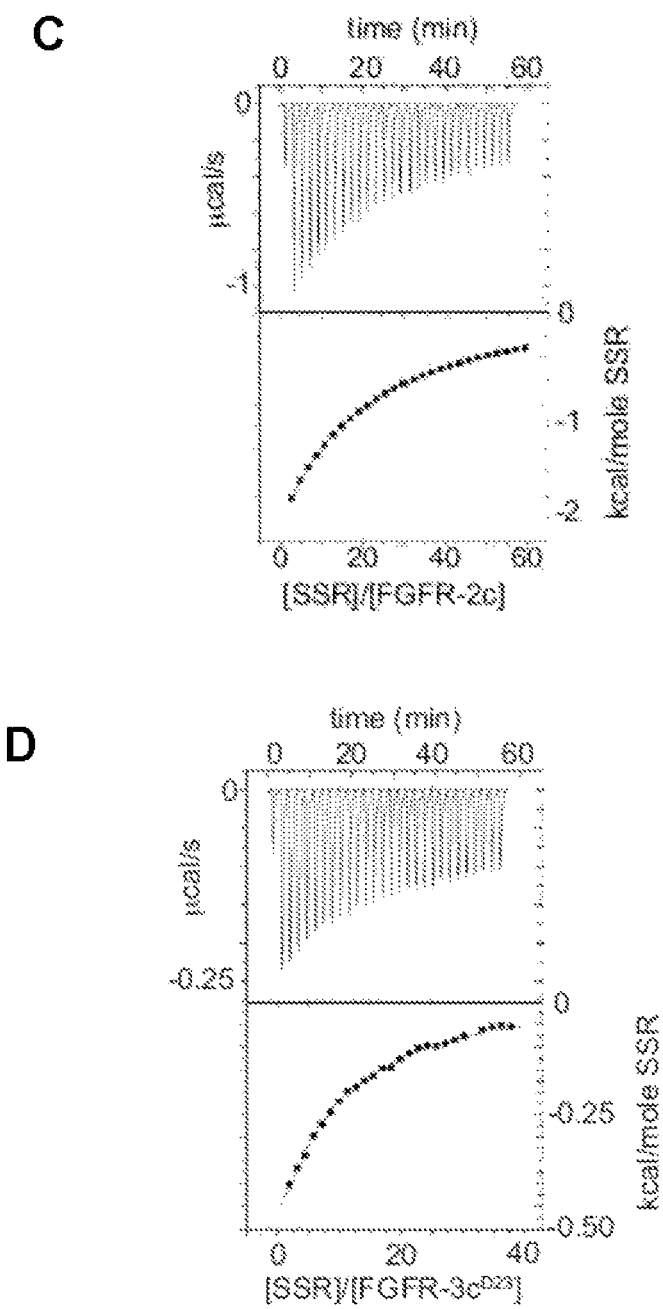

SSR128129E Binds to an Allosteric Site in the Ig-Like Domain D3 of Extracellular Region of FGFRs Since SSR was a multi-FGFR inhibitor, we used polypeptide fragments of the various (human) FGFR subtypes. Saturation transfer difference NMR (STD-NMR) spectra of SSR revealed that SSR bound to the ECD of FGFR1 (FGFR1$^{3123}$) (FIG. 11A). This was confirmed by analysis of the one-dimensional (1D)-NMR profile, which revealed peak broadening of the FGFR1$^{3123}$ signal upon addition of SSR (FIG. 11A). This binding is specific because no binding is observed with TNF-R1 extracellular protein (FIG. 11A). We then used ECD fragments of FGFRs to map the binding site of SSR to one of the three Ig-domains. 1D-NMR measurements of a fragment containing only domain D3 (FGFR1$^{33}$) identified a binding site for SSR in this juxta-membrane domain (FIG. 11B). In fact, FGFR1$^{33}$ and FGFR1$^{3123}$ give identical signals (broad line) meaning that we obtained same affinity for these proteins while FGFR1$^{312}$ and FGFR1$^{32}$ cause sharp lines (FIG. 11B). Isothermal titration calorimetry (ITC), using two ECD fragments, FGFR2$^{323}$ (consisting of domain D2 and 3) and FGFR3$^{323}$ revealed that SSR bound to FGFR2 and FGFR3 (FIGS. 11C and 11D).

Figure 12:
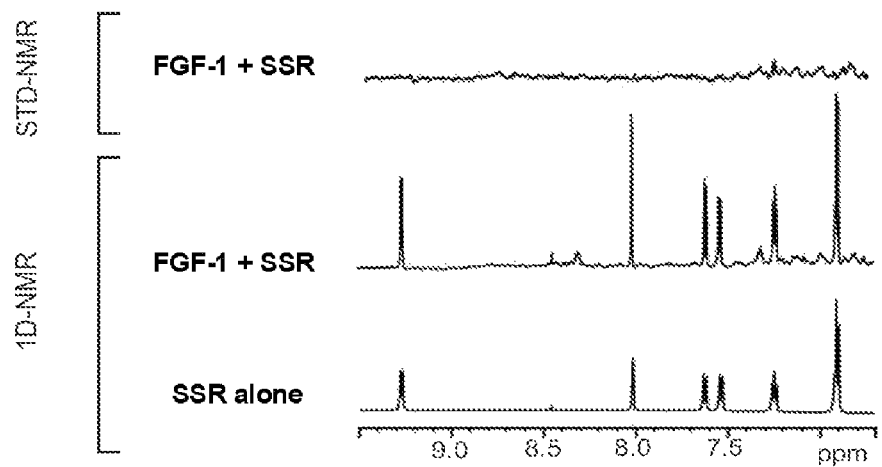
FIG. 12: NMR (A, C) and ITC (B) studies demonstrating that SSR is not able to interact with FGF1 (A, B) and FGF2 (C). D/ No interference in SSR binding on FGFR1 is observed following addition of sucrose octasulfate (SOS), a heparin mimetics, confirming that SSR doesn't interact with heparin binding site of FGFR1.
Figure 12:
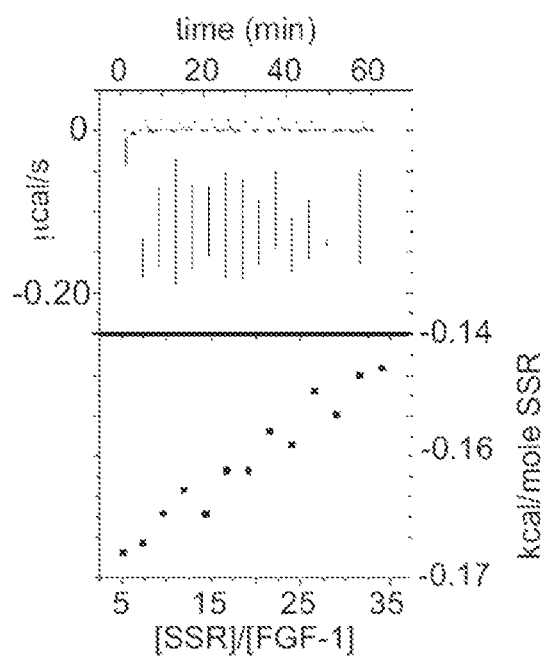
Figure 12:
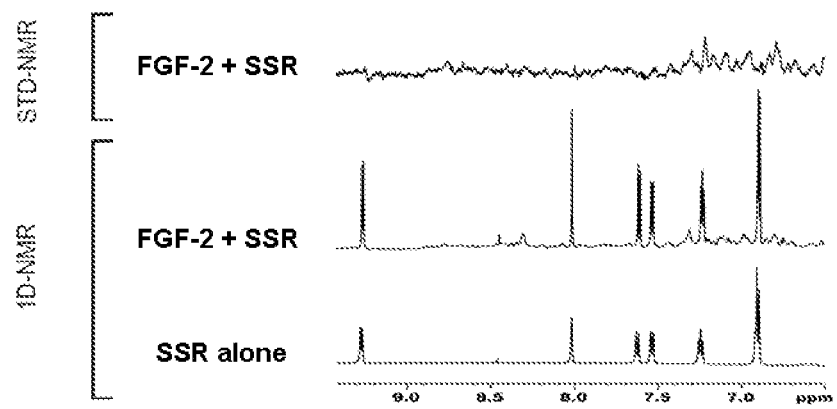
Figure 12:
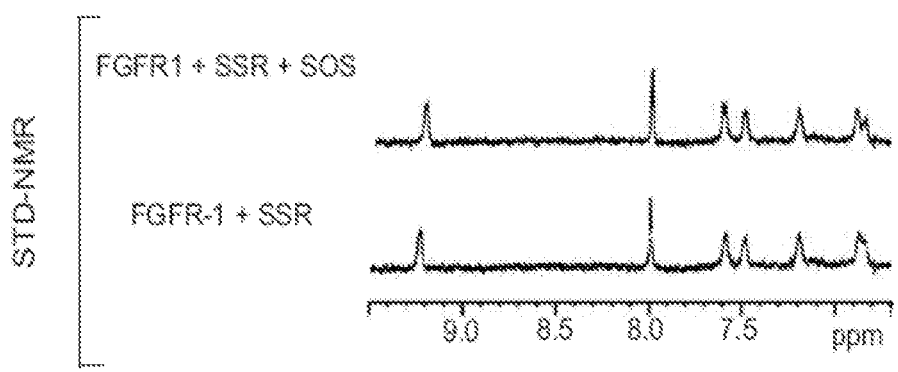

The binding of SSR to domain D3 of FGFRs was specific, as the compound failed to bind to FGF-ligands (FGF1 and FGF2; FIGS. 12A, 12B and 12C) when analyzed by ITC or STD-NMR. Moreover, heparin did not interfere with the binding of SSR to FGFR, as STD-NMR revealed a comparable signal of SSR to the FGFR in either the presence or absence of the heparin analogue sucrose octasulphate (SOS, FIG. 12D).

Example 5

Allosteric Binding of SSR Induces Conformational Change in FGFR

We then explored whether we could obtain direct evidence of a conformational change of the FGFR mediated by the binding of SSR to the region identified in the preceding experiments. Therefore, we performed Fourier transform infrared (FTIR) spectroscopic measurements of ECD fragments of FGFR2, consisting of domains domains D2-3 (FGFR2$^{323}$). Addition of SSR to either variant resulted in an increase in the amplitude of the amide I band of the FTIR spectrum with a maximum around 1,640 cm$^{-1}$, consistent with a global conformational change (FIG. 12A).

Figure 13:
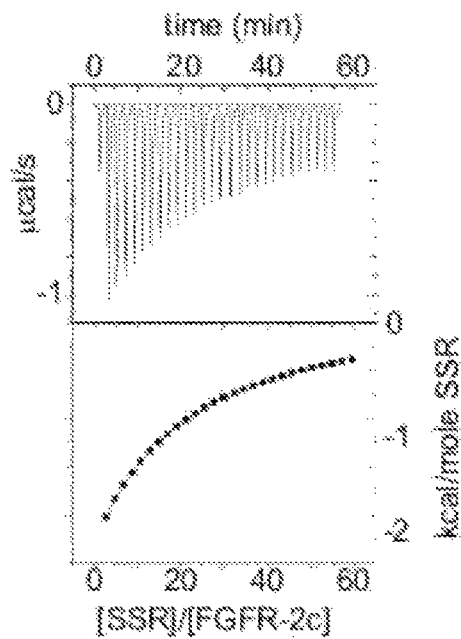
FIG. 13: In silico modeling and mutagenesis identify allosteric binding site for SSR near the Y328 amino acid. ITC experiments on WT FGFR2 extracellular domain (A) show interaction between SSR and FGFR2. This binding failed when measurements are realized with Y328D mutant (B) confirm that Y328D mutation renders FGFR2 insensitive to SSR binding.
Figure 13:
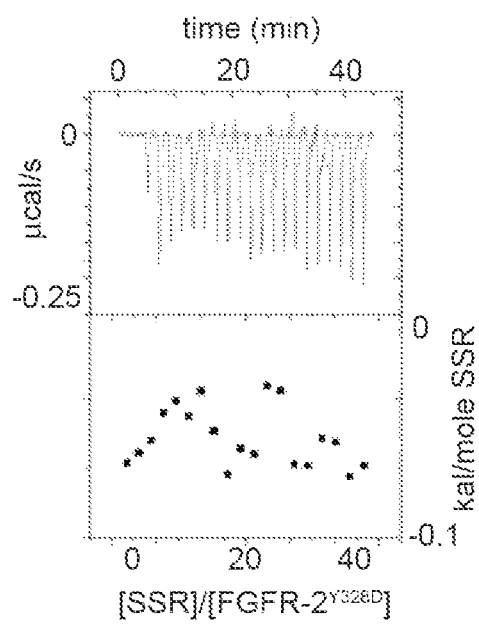
Figure 14:
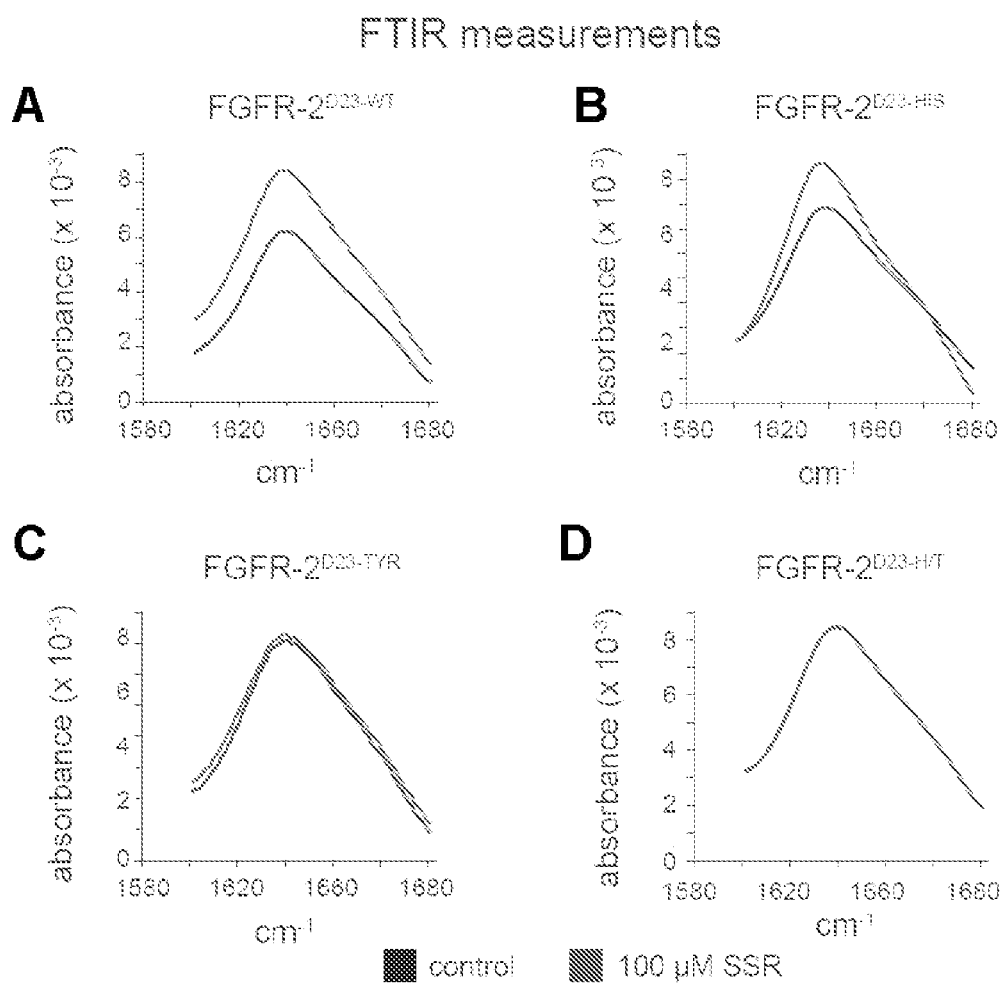
FIG. 14: Fourier Transform InfraRed (FTIR) measurements of purified (A) FGFR2δ23-WT, (B) FGFR2-δ23-His, (C) FGFR2-δ23-Tyr, (D) FGFR2-δ23-H/T (H295L/Y328D double mutant) without or with 100 μM SSR (black and grey line respectively) identified a conformational change in both WT or His295L mutant while mutating Y328D renders FGFR2 insensitive for this change.

We next explored whether SSR bound to amino acid residues that form part of the orthosteric site in D3 or to an alternative allosteric site. Initially, we used the molecular docking algorithms of the software packages MOLEGRO, Autodock and YASARA and available crystallographic data. Docking runs of SSR on FGFR2$^{D3}$ using both methods identified two putative binding sites, one centered around His$^{293}$ and another around Tyr$^{328}$; these putative binding sites are, relative to the FGF ligand binding site, located at the opposite face of the receptor and form a hydrophobic pocket ~25 Å from the orthosteric binding site. Notably, both residues do not overlap with residues of the orthosteric FGF binding pocket. To evaluate the functional relevance of both putative SSR binding sites, we used the molecular forcefield FoldX software (Schymkowitz et al., 2005) to design mutations that would reduce or eliminate allosteric ligand binding, without, however, perturbing the overall conformational stability of the structure: (i) FGFR2$^{D3-Y328D}$, which removes a hydrophobic interaction with SSR by replacing the aromatic residue with a negatively charged aspartate; (ii) FGFR2$^{D234-H293L}$, which removes a critical residue from the other putative binding site for SSR; and (iii) the FGFR2$^{D3-Y328D/H293L}$ double mutant (referred to as FGFR2$^{D3-YH}$). ITC binding experiments showed that SSR failed to bind to FGFR2$^{D3-Y328D}$ (FIGS. 13B and 13C). These findings are consistent with a model whereby SSR binds to an allosteric site formed by a hydrophobic pocket near the orthosteric ligand binding site, and in which residue Tyr$^{328}$ seems to be critical for mediating the interaction between SSR to FGFR2. We also analyzed the FTIR spectrum of the aforementioned mutated FGFR2 fragments. None of these single or double mutations induced a major shift in the FTIR spectrum, indicating that the overall three-dimensional configuration of these FGFR variants was comparable. SSR induced a comparable shift of the FTIR spectrum of FGFR2$^{D3-H293L}$ and the native FGFR2$^{D3}$ fragment (FIGS. 14A and 14B) suggesting that mutation His293 to Leu293 isn't sufficiently drastic or that His293 is not so much implied in interaction with SSR. In contrast, SSR failed to induce this change in the FTIR spectrum of the mutated FGFR2$^{D3-Y328D}$ or FGFR2$^{D3-YH}$ fragments (FIGS. 14C and 14D), indicating that residue Tyr$^{328}$ was indeed critical in mediating the allosteric conformational change of FGFR2 upon binding SSR.

Example 6

Figure 15:
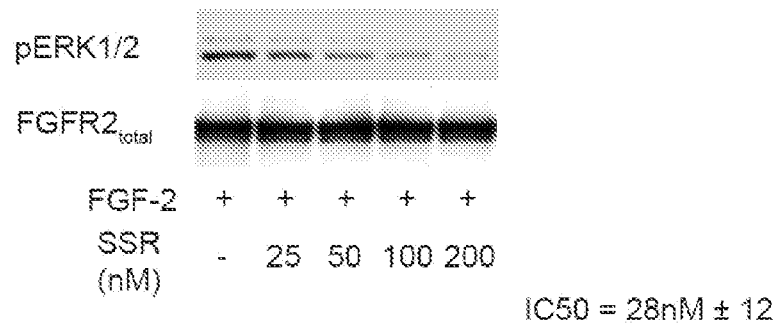
FIG. 15: Western blot analysis of activated Erk1/2, after stimulation with FGF2 (0.5 ng/ml for 5 min) of stably transfected HEK293 cells with full length FGFR2-WT or -Y328D. Densitometry defined IC50 value (average±sem; three independent experiments), show that the FGFR2-Y328D mutant receptor (B) is about 5 times less sensitive to SSR inhibition as compared to FGFR2-WT (A).
Figure 15:
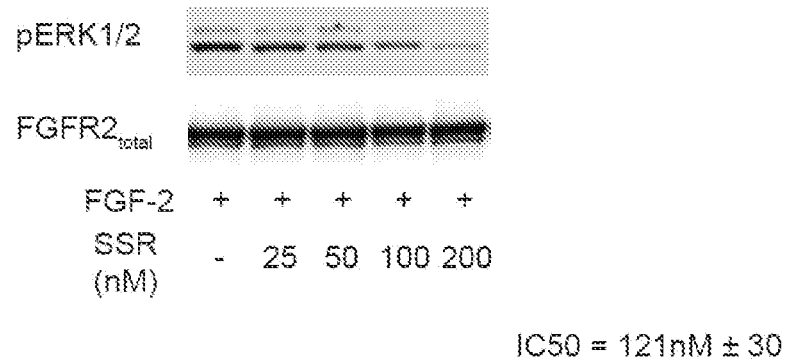

Mutation of the Allosteric SSR Binding Site Reduces SSR Inhibition of FGFR Signalling To assess the functional importance of the allosteric site in regulating FGFR signaling, we generated stable HEK293 cell lines expressing either a functional FGFR2$^{WT}$ or the FGFR2$^{D3-Y328D}$ variant, and analyzed whether SSR inhibited the activation of ERK1/2 by FGF2 in these cell lines. Immunoblotting revealed that inhibition of FGF2 induced ERK1/2 phosphorylation in FGFR2$^{D3-Y328D}$ cells by SSR was reduced (IC$_{50}$ value: 121±30 nM) relative to its inhibitory potency at the FGFR2$^{WT}$ cells (IC$_{50}$ value: 28±12 nM) (FIGS. 15A and 15B), indicating that this allosteric site is not only relevant for SSR binding to purified FGFR2 fragments in vitro, but also for its inhibitory activity on FGFR2 signaling in physiological conditions in cellulo. The fact that the Y$^{328}$D mutation did not completely abolish the inhibitory activity of SSR may suggest that other adjacent residues in addition to Tyr$^{328}$ also contribute to the binding of SSR when FGFR2 is expressed in a physiological context.

Example 7

SSR is a "Biased" Inhibitor of FGFR-Dependent Phospho-Signaling

Figure 16:
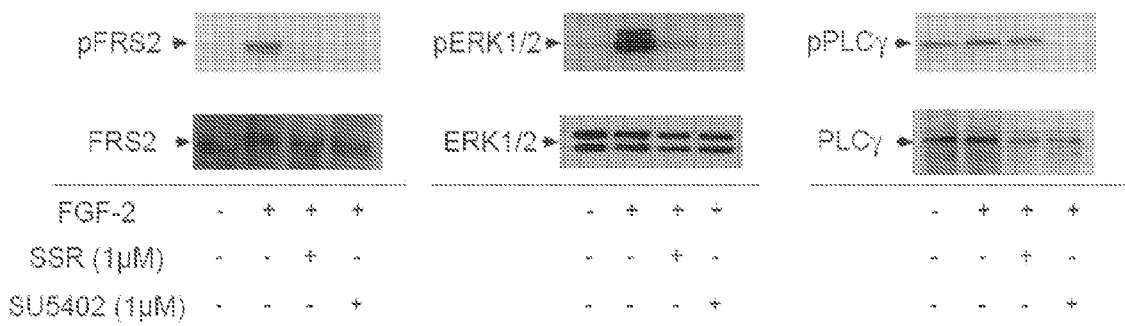
FIG. 16: A/ Western blot analysis of SSR effect compared to FGFR tyrosine kinase inhibitor SU5402 on FGFR2 transfected HEK cells stimulated with FGF2. SU5402 inhibits PLCγ, FRS2 and Erk1/2 phosphorylation while SSR doesn't inhibit PLCγ pathway indicating a biased antagonism by SSR (B).
Figure 16:
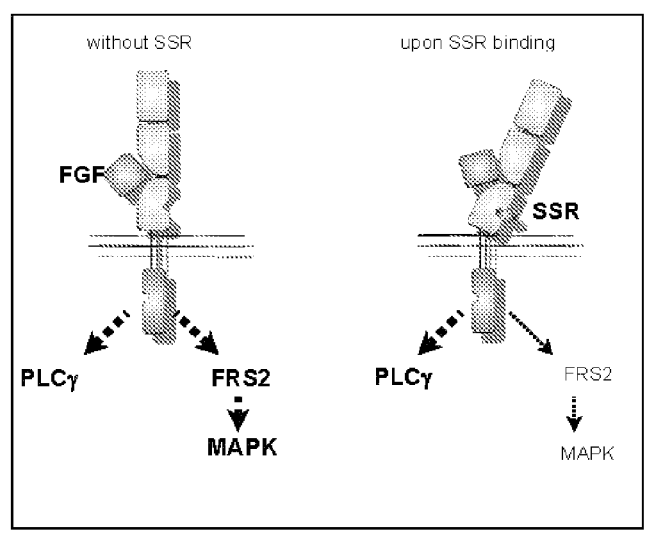

In order to evaluate SSR effect on FGFR-controlled phosphor-signalling, HEK293 cells have been transfected with FGFR2 and the two main pathways following FGFR autophosphorylation, PLCγ and FRS2, have been studied by western blot in comparison with a published FGFR tyrosine kinase inhibitor SU5402 described to inhibit FGFR-dependent FRS2 and PLCγ cascades (Zhen et al., Oncogene 2007). In such cells, FGF induces FRS2, Erk1/2 and PLCγ phosphorylation. SU5402 blocks all these inductions while SSR only inhibits FRS2 pathway (FIGS. 16A and 16B) illustrating the biased antagonism obtained with SSR. More generally, these differences in phosphorylation can be used as reporter to evaluate allosteric modulators.

Example 8

Methodology to Search for Frustrated Domain in Extracellular Domain of Tyrosine Kinase Receptors One of the possible molecular mechanisms of the described conformational change from example 5, involves the presence of a frustrated domain (see above for definition). When analyzing domains D2 and D3 of human FGFR2 using AGADIR (a helix stability prediction algorithm; Muñoz, V. & Serrano, L. 1994), we identified a sequence of residues, ranging from Tyr$^{319}$ to Arg$^{330}$, (thus including the critical residue Tyr$^{328}$) as the only region that is prone to undergo a shift from a β-sheet to an α-helix. In agreement with such theoretical model, replacement of Tyr$^{328}$ by aspartate (FGFR2$^{D3-Y328D}$)), which was predicted by AGADIR to reduce the alpha helicality and thus to reduce the frustration of the domain, indeed prevented the observed conformational change, as detected by FTIR analysis. Similar sequence analysis of additional growth factor receptors including VEGFR1, -2 &-3 and PDGFRβ, among other TKRs, contained regions of relatively high AGADIR scores, which could be reversed by mutating a critical residue from this region into aspartate. We have some preliminary data of VEGFR2 where mutating K609D and K648D resulted in reduced ERK1/2 signaling upon stimulation with VEGF.

Example 9

Affinity Screening of FGF-Rs Allosteric Modulators by SEC-LC/MS and Activity Evaluation of Identified Compounds The SEC-LC/MS methodoly is an analytical technique used for the affinity screening dependent on a 2-dimensional system coupled on-line: a size exclusion chromatography associated with a high performance liquid chromatography followed by an electrospray ionisation—time of flight mass spectrometry for detection.

It is based on the ability of some compounds to interact with soluble polypeptides (peptide, protein domain, or full length protein). Following the mixing of a pool of small compounds with the peptide of interest, the peptide-ligand complexe induces a mass shift allowing separation between unbound and bound small compounds by size exclusion chromatography. Then, complexes are dissociated and binders are detected using a high resolution LC/ESI-TOF for accurate mass measurement (for example with a Waters LCT Premier Mass Spectrometer). Data deconvolution algorithm allows identification of bound molecules from mass detection analysis.

For the identification of FGF-Rs allosteric modulators, this technology can be applied to the extracellular domain of different FGF-Rs, native or mutated. The native form allows the detection of all the extracellular domain binders. Another way to realize screening for allosteric modulators could be done by using "open" form of FGF-R2 helix close to the SSR128129 binding site obtained with mutations Tyr328Arg-Ile329Lys that stabilize alpha-helix allowing sensitization to SSR128129 binding. In this case, this mutated FGF-R2 can replace WT FGF-R2. A similar strategy can be used to carry out a screening on the FGF-R1, -R3 or -R4 with mutations at the amino acids corresponding to Tyr328 and Ile329 in FGF-R2. The mutated form at Tyr328 (FGF-R2) or corresponding mutated amino acids in others FGF-Rs can be used to make a counterscreen. Because, SSR128129 fails to bind on the FGF-R2, mutated at Tyr328Asp near a hydrophobic pocket, this mutated form can be used to discard part of compounds that don't interact with targeted pocket on FGF-R2.

Figure 17:
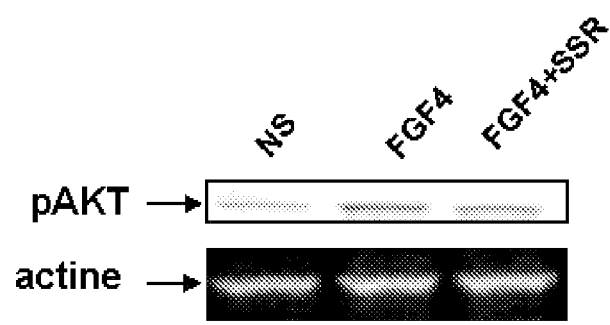
FIG. 17: Western blot analysis (A) of SSR effect on FGF2-induced AKT phosphorylation in HUVEC with the corresponding quantification graphe (B). C/ This effect is also quantifiable with an on-cells ELISA directed against phospho-AKT (Ser473). D/ This effect is independent on SSR unability to compete with FGF binding on FGFR.
Figure 17:
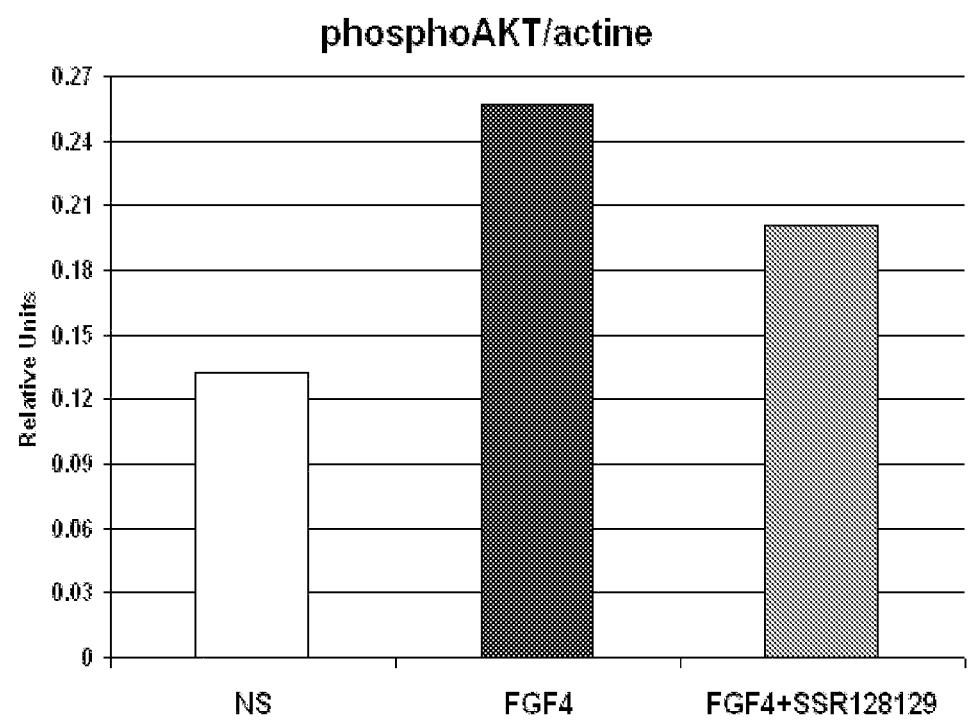
Figure 17:
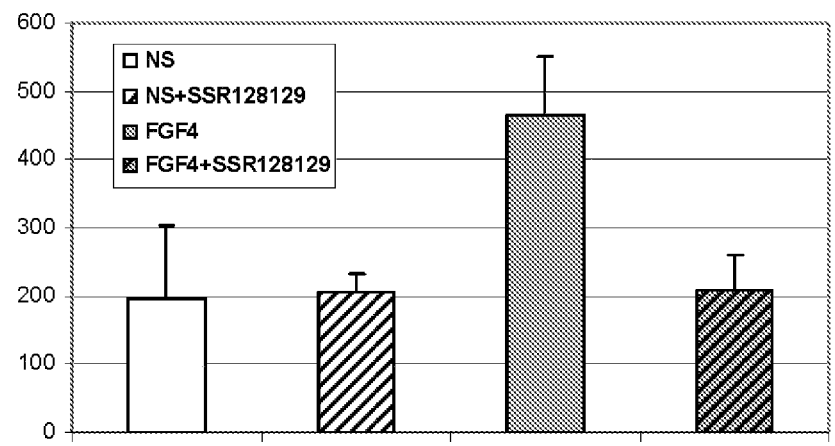
Figure 17:
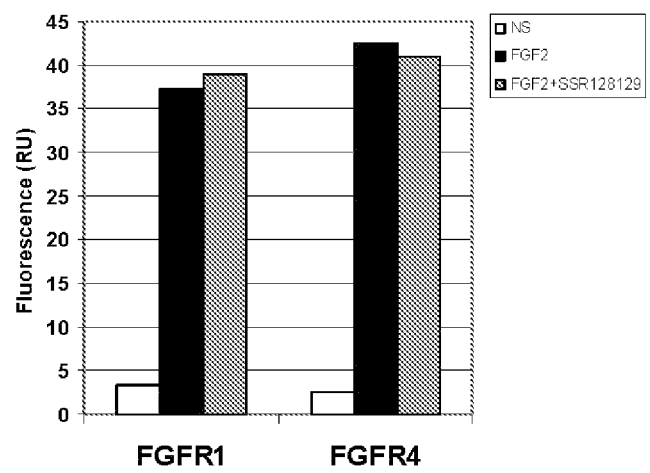

In all cases, this strategy leads to the identification of molecules able to bind on the target pocket in the peptide of interest. In a next step, the cellular effect has to be evaluated. First, the selected compounds have to inhibit an FGF-induced induced pathway, such as AKT phosphorylation in HUVEC cells, as observed with SSR in western-blot experiments (FIGS. 17A and 17B). The phosphorylation state of AKT in HUVEC cells can be measured by an on-cell ELISA methodology. This assay format has been developed in house for the direct detection of AKT phosphorylation in various cells such as HUVEC and allows the detection of SSR effect on FGF4-stimulated HUVEC (FIG. 17C). A typical feature of FGFR allosteric modulators is their inability to compete with FGF binding. In order to evaluate this, a binding assay on murine pre-B 300-19 cells transfected with FGFRs has been elaborated. AlexaFluor488-labelled FGF2 at 10 ng/ml binds to FGFR1 or FGFR4 expressed on 300-19 cells that naturally don't express any FGFR, and SSR at 300 nM is not able to compete this binding on FGFR1 or FGFR4 by flow cytometry analysis (FIG. 17D).

Example 10

Figure 18:
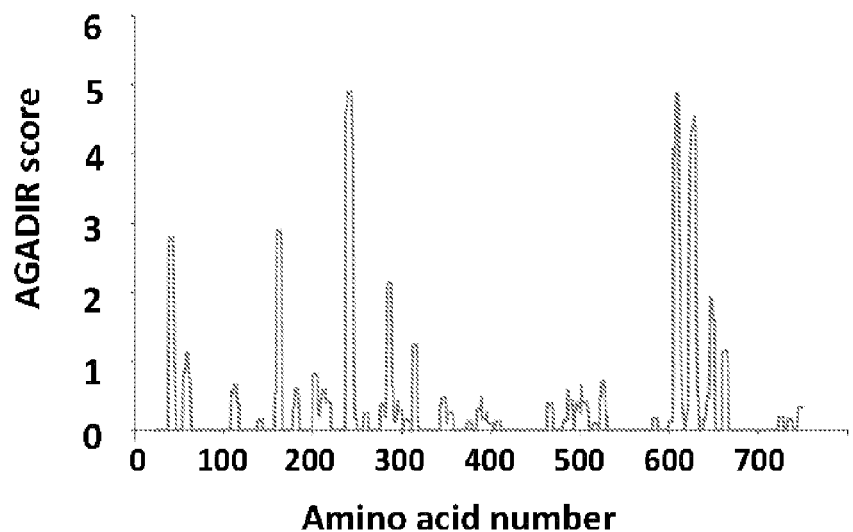
FIG. 18: Identification of putative frustrated zones in the VEGF-R2 receptor using software program AGADIR and mutation analysis. (A) Some regions that are prone to undergo structural changes (e.g. β-sheet to α-helix transitions) have been identified by. (B) Two lysines (K609 and K648) have been choosen for mutation into Aspartate due to their closeness to transmembrane domain and their most negative impact on helicity property following mutation.
Figure 18:
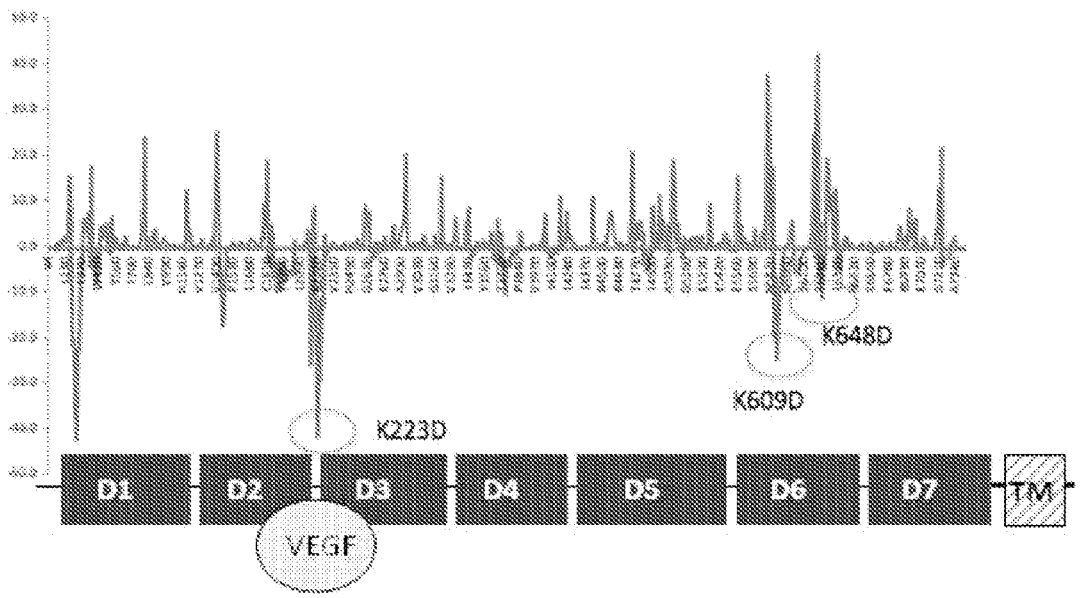

Identification of Putative Frustrated Zones in the VEGF-R2 Receptor and Mutation Analysis of the Putative Frustrated Zones The strategy developed for FGF-Rs is applied to another receptor TK: VEGF-R2 or KDR. As an initial approach to identify regions that could harbor putative allosteric target sites, we utilized the software program AGADIR[1] to identify regions that are prone to undergo structural changes (e.g. β-sheet to α-helix transitions), employing available primary amino acid sequences from the murine VEGF-R2 receptor (Entrez accession NP_034742.2). This resulted in several regions with a higher helical propensity, though in the Ig-domain structure mainly β-sheet structures should be expected. The results of the Agadir analysis are shown in FIG. 18A.

Subsequently, after in silico mutating each amino acid from VEGF-R2 sequentially by an aspartate residue (D), we analyzed the AGADIR score again and selected those mutations (i) from which the change in helical propensity was largest (most negative) and (ii) that were located in those Ig-domains located nearest to the trans-membrane domain. From these, K609D and K648D, both residues residing in domain IgD6 of mVEGF-R2 (FIG. 18B), yielded the largest reduction in helical propensity and were further used for in cellulo analysis (see further example 12).

Example 11

Figure 19:
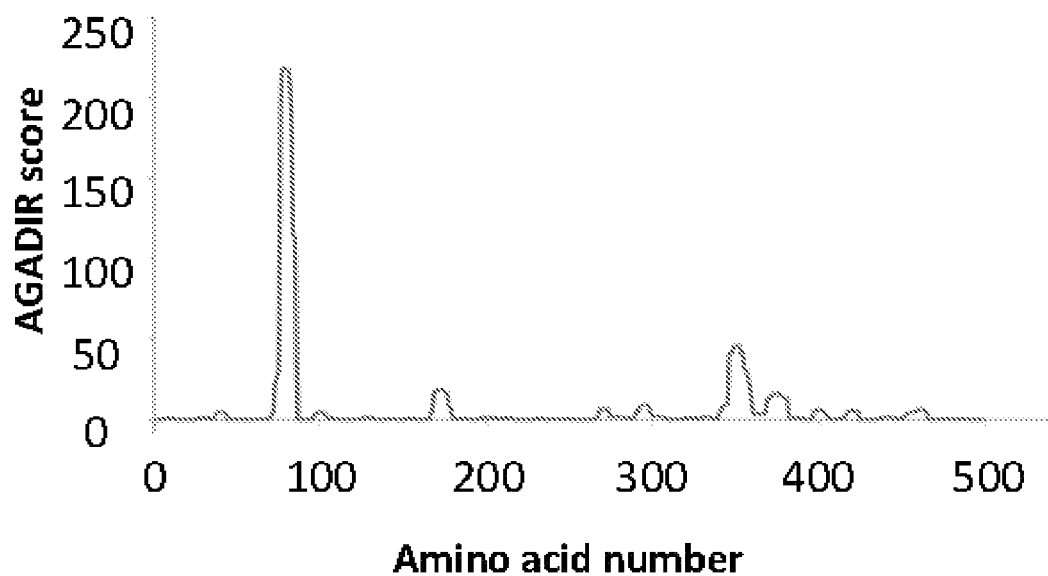
FIG. 19: Identification of putative frustrated zones in the PDGF-Rβ receptor using software program AGADIR and mutation analysis. Mutations Lysine387 into Aspartate and Leucine383 into aspartate seem to have the most negative impact on helicity property.

Identification of Putative Frustrated Zones in the PDGF-RR Receptor and Mutation Analysis of the Putative Frustrated Zones As an initial approach to identify regions that could harbor putative allosteric target sites, we utilized the software program AGADIR[1] to identify regions that are prone to undergo structural changes (e.g. β-sheet to α-helix transitions), employing available primary amino acid sequences from the human PDGFRR receptor (Entrez accession NP_002600.1). This resulted in several regions with a higher helical propensity, though in the Ig-domain structure mainly β-sheet structures should be expected (FIG. 19). Subsequently, after in silico mutating each amino acid from PDGFRβ sequentially by an aspartate residue (D), we analyzed the AGADIR score again and selected those mutations (i) from which the change in helical propensity was largest (most negative) and (ii) that were located in those Ig-domains located nearest to the trans-membrane domain. From these, L383D and K387D, both residues residing in domain IgD3 of hPDGFRβ, yielded the largest reduction in helical propensity (FIG. 19).

Example 12

Screening Method to Identify Compounds Inducing a "Biased" Signaling

Figure 20:
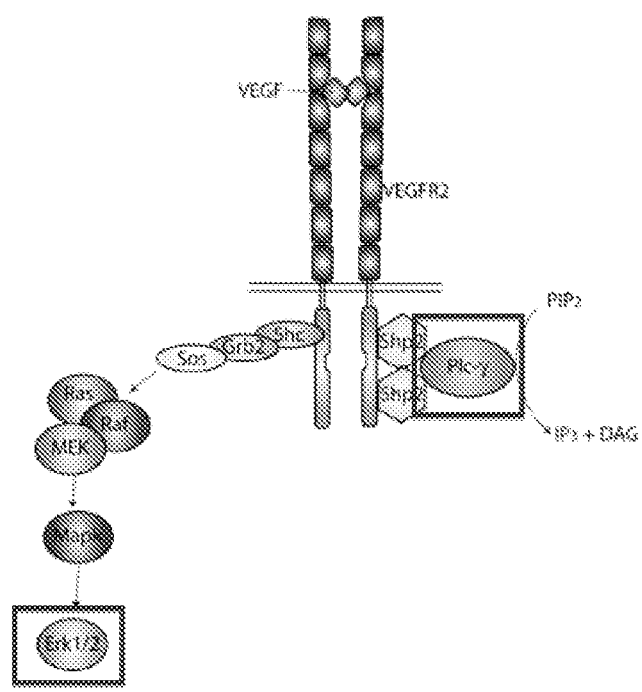
FIG. 20: Schematic representation of VEGF-R2 and PDGF-Rβ receptors signaling pathways activation through Erk1/2 and PLCγ. (A) VEGFR2 signalling following VEGF stimulation and (B) PDGF-Rβ signalling following PDGF stimulation.
Figure 20:
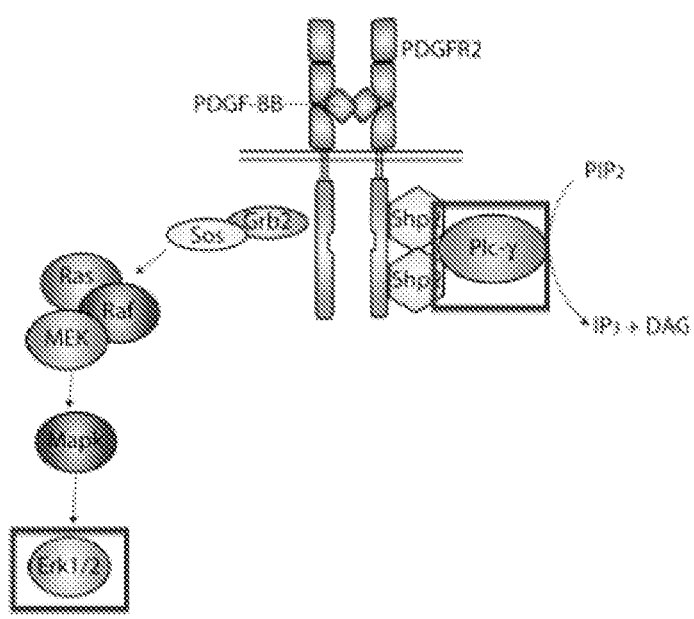

Binding of VEGF or PDGF-BB induces dimerization of the respective cognate receptors, which, on its turn, induces phosphorylation of the intracellular kinase domains. Subsequently two major pathways (of interest in accordance with FGF-Rs biased antagonist SSR) are activated including the ERK1/2 pathway (FIGS. 21A and 21C) and the PLCγ pathway (schematically represented in FIG. 20). Measuring the activation of each of the pathways, in presence or absence of a possible inhibitor, leads to the indentification of compounds inducing a "biased" signaling, by inhibition of only one of the signaling pathways.

For VEGF-R2, the two mutant VEGFR2 receptors (VEGFR2$^{K609D}$ and VEGFR2$^{K648D}$) identified in example 10 and the wilt type form of VEGF-R2 were stably expressed in HEK293 cells. The VEGFR2$^{WT}$ receptor clearly responds by activating ERK1/2 phosphorylation. While the VEGFR2$^{K609D}$ mutant has a reduced signaling capability through ERK1/2 (but sufiscient for a counterscreening assay), the VEGFR2$^{K648D}$ mutant lost it. The results are summarized in FIG. 21A.

Figure 21:
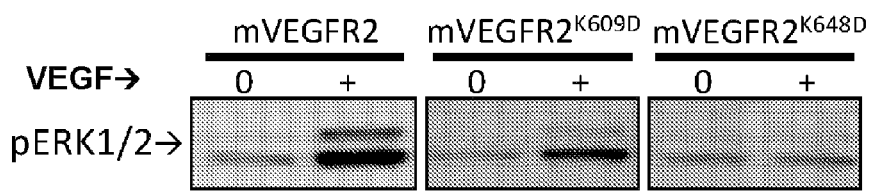
FIG. 21: Erk1/2 phosphorylation detection in HEK293 cells that overexpressed wild type or mutated forms of VEGF-R2 or PDGF-Rβ receptors using western blot or surefire assay. (A) mouse wild type for VEGF-R2 and mutated at K609D or K648D were stably transfected in HEK293 cells. Following starvation and stimulation without (0) or with (+) mouse VEGF, Erk1/2 phosphorylation is detected by Western blot. (B) schematic representation of the surefire assay to detect Erk1/2 (left scheme) or PLCγ (right scheme) phosphorylation on protein extracts. (C) Alphascreen surefire dosages of total or phosphorylated Erk1/2 in PDGFRβ-transfected HEK293 cells following stimulation with 10% FBS, 1 or 50 ng/ml PDGF-BB or without stimulation as control (0).
Figure 21:
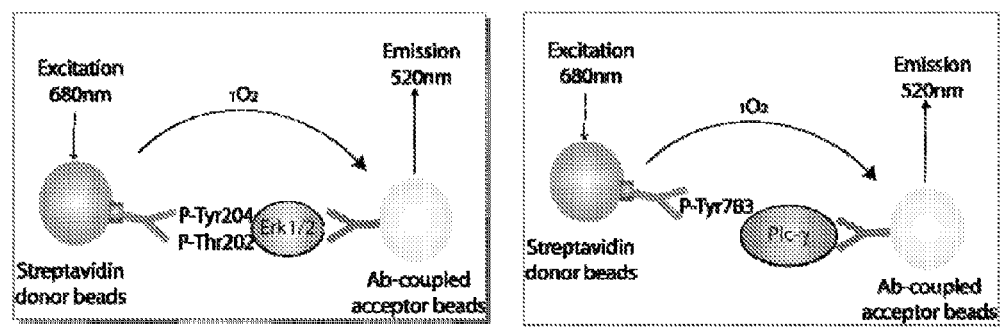
Figure 21:
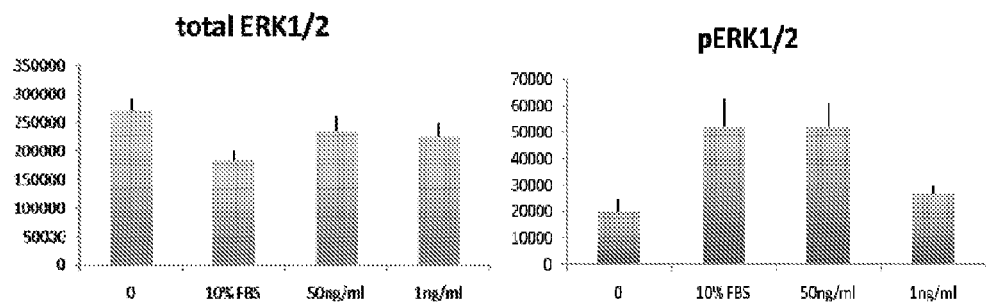

For PDGF-Rβ, the HEK293 cells overexpressing hPDGFRβ cells were stimulated either with medium containing no additives ("0"), 10% fetal bovine serum (10% FBS), 50 ng/ml PDGF-BB (50 ng/ml) or 1 ng/ml PDGF-BB (1 ng/ml) according to the alphascreen surfire procedure (FIG. 21B). In FIG. 21C, the left panel denotes again the schematic representation of the mixtures to detect the activated or total ERK1/2 proteins upon stimulation. The right panels denote the detected measurements following PDGF-BB stimulation of the cells as measured through the alphascreen surefire detection method. This shows that a clear signal can be detected when the cells are stimulated with either 10% FBS or 50 ng/ml of PDGF-BB, while a much lower signal is present without or with 1 ng/ml stimulation with PDGF-BB. The PLCγ answer is measured in a similar way.

A screening method for identifying compounds inducing a "biased" signaling on VEGF-R2 or PDGF-Rβ, like SSR on FGF-Rs, can be based on Erk1/2 and PLCγ answer. Comparing the ERK1/2 and the PLCγ response in presence and absence of candidate allosteric inhibitors allows the identification of compounds that act as a biased inhibitor: inhibiton only one of the two signaling pathways. The mutated constructs of VEGF-R2 or PDGF-Rβ may serve for a counter-screening assay to verify the mechanism of action of identified allosteric modulators. On the mutated receptors, compounds have to lose their receptor modulation capability.

REFERENCES

Barth, A. Selective monitoring of 3 out of 50 000 protein vibrations. *Biopolymers* 67, 237-241 (2002).

Beenken, A. & Mohammadi, M. The FGF family: biology, pathophysiology and therapy. *Nature reviews* 8, 235-253 (2009).

Bossard, C., et al. Antiangiogenic properties of fibstatin, an extracellular FGF-2-binding polypeptide. *Cancer Res* 64, 7507-7512 (2004).

Callarts-Vegh et al., *J Neurosci.* 26, 6573-6582 (2006)

Carmeliet, P. Angiogenesis in life, disease and medicine. *Nature* 438, 932-936 (2005).

Casanovas, O., Hicklin, D. J., Bergers, G. & Hanahan, D. Drug resistance by evasion of antiangiogenic targeting of VEGF signaling in late-stage pancreatic islet tumors. *Cancer Cell* 8, 299-309 (2005).

Cenni, E., et al. Inhibition of angiogenic activity of renal carcinoma by an antisense oligonucleotide targeting fibroblast growth factor-2. *Anticancer Res* 25, 1109-1113 (2005).

Christopoulus, A., Allosteric binding sites on cell surface receptors: novel targets for drug discovery. *Nat. Rev. Drug Discov.* 1, 198-210 (2002).

Christopoulus, A. and Kenakin, T. G protein coupled receptor, allosterism and complexing. *Pharmacol. Rev.* 54, 323-374 (2002).

Compagni, A., Wilgenbus, P., Impagnatiello, M. A., Cotten, M. & Christofori, G. Fibroblast growth factors are required for efficient tumor angiogenesis. *Cancer Res* 60, 7163-7169 (2000).

Crump, J. G., Maves, L., Lawson, N. D., Weinstein, B. M. & Kimmel, C. B. An essential role for Fgfs in endodermal pouch formation influences later craniofacial skeletal patterning. *Development* 131, 5703-5716 (2004).

Dimitroff, C. J., et al. Anti-angiogenic activity of selected receptor tyrosine kinase inhibitors, PD166285 and PD173074: implications for combination treatment with photodynamic therapy. *Invest New Drugs* 17, 121-135 (1999).

Eswarakumar, V. P., Lax, I. & Schlessinger, J. Cellular signaling by fibroblast growth factor receptors. *Cytokine Growth Factor Rev* 16, 139-149 (2005).

Furihata, K., Shimotakahara, S. And Tashiro, M. An efficient use of the WATERGATE W5 sequence for observing a ligand binding with a protein receptor. *Magn. Reson. Chem.* 46, 799-802 (2008).

Ghabrial, A. S. & Krasnow, M. A. Social interactions among epithelial cells during tracheal branching morphogenesis. *Nature* 441, 746-749 (2006).

Grassot, J., Gouy, M., Perriere, G. & Mouchiroud, G. Origin and molecular evolution of receptor tyrosine kinases with immunoglobulin-like domains. *Molecular biology and evolution* 23, 1232-1241 (2006).

Innis, C. A. & Hyvonen, M. Crystal structures of the heparan sulfate-binding domain of follistatin. Insights into ligand binding. *J Biol Chem* 278, 39969-39977 (2003).

Kenakin, T. et al. Seven transmembrane receptors as shape-shifting proteins: the impact of allosteric modulation and functional selectivity on new drug discovery. *Pharmacol rev*, 62, 265-304 (2010).

Kubo, H., et al. Blockade of vascular endothelial growth factor receptor-3 signaling inhibits fibroblast growth factor-2-induced lymphangiogenesis in mouse cornea. *Proc Natl Acad Sci USA* 99, 8868-8873 (2002).

Lavine, K. J., et al. Fibroblast growth factor signals regulate a wave of Hedgehog activation that is essential for coronary vascular development. *Genes & development* 20, 1651-1666 (2006).

Leach, K., Sexton, P. M. and Christopoulos, A. Allosteric GPCR modulators: taking advantage of permissive receptor pharmacology. *Trends Pharmacol. Sci.* 28, 382-389 (2007).

Litschig, S. et al., CPCCOEt, a non competitive metabotropic glutamate receptor 1 antagonist inhibits receptor signalling without afeecting glutamate binding. *Mol. Pharmacol.* 55, 453-461 (1999).

Malemud, C. J. Growth hormone, VEGF and FGF: involvement in rheumatoid arthritis. *Clinica chimica acta; international journal of clinical chemistry* 375, 10-19 (2007).

May, L. T., Leach, K., Sexton, P. M. and Christopoulos, A. Allosteric modulation of G protein-coupled receptors. *Annu. Rev. Pharmacol. Toxicol.* 47, 1-51 (2007).

McDermott, L. A., et al. RO4383596, an orally active KDR, FGFR, and PDGFR inhibitor: synthesis and biological evaluation. *Bioorg Med Chem* 13, 4835-4841 (2005).

Muñoz, V. & Serrano, L. (1994) Elucidating the folding problem of helical peptides using empirical parameters. *Nature Struct. Biol.* 1, 399-409 (1994)

Nagendra, H. G., et al. Sequence analyses and comparative modeling of fly and worm fibroblast growth factor receptors indicate that the determinants for FGF and heparin binding are retained in evolution. *FEBS letters* 501, 51-58 (2001).

Ornitz, D. M. & Marie, P. J. FGF signaling pathways in endochondral and intramembranous bone development and human genetic disease. *Genes & development* 16, 1446-1465 (2002).

Overington, J. P., Al-Lazikani, B., and Hopkins, A. L. How many drug targets are there? *Nat. Rev. Drug Discov.* 5, 993-995 (2006).

Pellegrini, L., Burke, D. F., von Delft, F., Mulloy, B. & Blundell, T. L. Crystal structure of fibroblast growth factor receptor ectodomain bound to ligand and heparin. *Nature* 407, 1029-1034 (2000).

Presta, M., et al. Fibroblast growth factor/fibroblast growth factor receptor system in angiogenesis. *Cytokine Growth Factor Rev* 16, 159-178 (2005).

Price, M. R. et al. Allosteric modulation of the cannabinoid CB1 receptor. *Mol. Phatrmacol.* 68, 1484-1495 (2005).

Rost, B. Rising accuracy of protein secondary structure perediction. In <<Protein structure determination, analysis and modeling for drug discovery, pp 207-249. (ed. D. Chasman, New York, Dekker, 2003)

Schymkowitz, J., et al. The FoldX web server: an online force field. *Nucleic acids research* 33, W382-388 (2005).

Shin, J. W., et al. Prox1 promotes lineage-specific expression of fibroblast growth factor (FGF) receptor-3 in lymphatic endothelium: a role for FGF signaling in lymphangiogenesis. *Mol Biol Cell* 17, 576-584 (2006).

Urban J. D., et al. Functional selectivity and classical concepts of quantitative pharmacology. *J. Pharmacol. Exp. Ther.* 320, 1-13 (2007).

The invention claimed is:

1. A method for identifying an allosteric inhibitor of a receptor tyrosine kinase (RTK) comprising the steps of:
   a) contacting an allosteric binding site of a RTK with a small compound allosteric inhibitor candidate compound;
   b) measuring the state of at least one reporter for the ERK1/2 signalling pathway and the state of at least one reporter for the PLCγ signalling pathway before and after the contacting step (a);
   c) comparing any changes in the state of the at least one reporter for each of the ERK1/2 signalling pathway and the PLCγ signaling pathway induced by the contacting step (a); and
   d) identifying an allosteric inhibitor of the RTK when, in the presence of the small compound allosteric inhibitor candidate compound bound to the allosteric binding site of the RTK, one of the ERK1/2 or PLCγ signalling pathway is inhibited and the other pathway is unaffected.

2. The method of claim 1, wherein the small compound has a molecular weight of less than 1000 D, less than 900 D, less than 800 D, less than 700 D, less than 600 D or less than 500 D.

3. The method of claim 1, wherein the RTK is selected from the group consisting of Platelet Derived Growth Factor Receptor (PDGFR), Fibroblast Growth Factor Receptor (FGFR), Vascular Endothelial Growth Factor Receptor (VEGFR), Tyrosine kinase Receptor (TrkR), AXL tyrosine kinase Receptor (AXLR), TIE Receptor (TIER), Retinoid-related Orphan Receptor (ROR), Protein Tyrosine Kinase 7 Receptor (PKT7R), and Muscle-Specific Kinase Receptor (MuSKR).

4. The method of claim 3, wherein the RTK is FGFR.

5. The method of claim 4, wherein the at least one reporter for the ERK1/2 signalling pathway is ERK1/2 phosphorylation or ERK1/2 dephosphorylation.

6. The method of claim 4, wherein the at least one reporter for the PLCγ signalling pathway is PLCγ phosphorylation or PLCγ dephosphorylation.

7. A method for identifying an allosteric inhibitor of a RTK comprising the steps of:
   a) contacting an allosteric binding site of a RTK with a small compound allosteric inhibitor candidate compound;
   b) measuring the ERK1/2 signalling pathway by determining the phosphorylation state of ERK1/2 and measuring the PLCγ signalling pathway by determining the phosphorylation state of PLCγ before and after the contacting step (a);
   g) comparing any changes in the phosphorylation states of ERK1/2 and PLCγ for each of the ERK1/2 signalling pathway and the PLCγ signalling pathway induced by the contacting step (a); and
   d) identifying an allosteric inhibitor of the RTK when, in the presence of the small compound allosteric inhibitor candidate compound bound to the allosteric binding site of the RTK, one of the ERK1/2 or PLCγ signalling pathway is inhibited and the other pathway is unaffected.

8. The method of claim 7, wherein the small compound has a molecular weight of less than 1000 D, less than 900 D, less than 800 D, less than 700 D, less than 600 D or less than 500 D.

9. The method of claim 7, wherein the RTK is selected from the group consisting of PDGFR, FGFR, VEGFR, TrkR, AXLR, TIER, ROR, PKT7R, and MuSKR.

10. The method of claim 9, wherein the RTK is FGFR.

11. A method for identifying an allosteric inhibitor of a FGFR comprising the steps of:
- e) contacting an allosteric binding site of a FGFR with a small compound allosteric inhibitor candidate compound;
- f) measuring the ERK1/2 signalling pathway by determining the phosphorylation state of ERK1/2 and measuring the PLCγ signalling pathway by determining the phosphorylation state of PLCγ before and after the contacting step (e);
- g) comparing any changes in the phosphorylation states of ERK1/2 and PLCγ for each of the ERK1/2 signalling pathway and the PLCγ signalling pathway induced by the contacting step (e); and
- h) identifying an allosteric inhibitor of the FGFR when, in the presence of the small compound allosteric inhibitor candidate compound bound to the allosteric binding site of the FGFR, one of the ERK1/2 or PLCγ signalling pathway is inhibited and the other pathway is unaffected.

* * * * *